US010856730B2

(12) United States Patent
Nakanishi

(10) Patent No.: US 10,856,730 B2
(45) Date of Patent: Dec. 8, 2020

(54) MEDICAL LIGHT SOURCE DEVICE AND MEDICAL ENDOSCOPIC DEVICE

(71) Applicant: Sony Olympus Medical Solutions Inc., Tokyo (JP)

(72) Inventor: Tatsuya Nakanishi, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 119 days.

(21) Appl. No.: 16/149,824

(22) Filed: Oct. 2, 2018

(65) Prior Publication Data

US 2019/0125175 A1 May 2, 2019

(30) Foreign Application Priority Data

Oct. 27, 2017 (JP) .................................. 2017-208495

(51) Int. Cl.
| | |
|---|---|
| *A61B 1/06* | (2006.01) |
| *F21K 9/60* | (2016.01) |
| *A61B 1/04* | (2006.01) |
| *A61B 1/12* | (2006.01) |

(52) U.S. Cl.
CPC .............. *A61B 1/0638* (2013.01); *A61B 1/04* (2013.01); *A61B 1/0646* (2013.01); *A61B 1/0669* (2013.01); *A61B 1/0676* (2013.01); *A61B 1/128* (2013.01); *F21K 9/60* (2016.08)

(58) Field of Classification Search
None
See application file for complete search history.

(56) References Cited

U.S. PATENT DOCUMENTS

| | | | |
|---|---|---|---|
| 2013/0242595 A1* | 9/2013 | Jaffe | F21V 11/00 362/552 |
| 2017/0156577 A1* | 6/2017 | Machida | A61B 1/0669 |
| 2017/0293134 A1* | 10/2017 | Otterstrom | G02B 23/2461 |
| 2019/0090726 A1* | 3/2019 | Park | A61B 1/00186 |

FOREIGN PATENT DOCUMENTS

WO    WO 2015/016172 A1    2/2015

* cited by examiner

*Primary Examiner* — Sharon E Payne
(74) *Attorney, Agent, or Firm* — Xensus LLP

(57) ABSTRACT

A medical light source device includes: a first solid state light emitting element configured to emit first color light; a second solid state light emitting element configured to emit second color light; a third solid state light emitting element configured to emit third color light; a fourth solid state light emitting element configured to emit fourth color light; and a color synthesis optical device configured to synthesize the first color light, the second color light, the third color light, and the fourth color light. The color synthesis optical device includes a first color separation surface, a second color separation surface disposed to intersect with the first color separation surface, and a third color separation surface disposed on a light path latter stage with respect to the first color separation surface and the second color separation surface.

12 Claims, 13 Drawing Sheets

FIG.9

| | AR-RANGE-MENT (1) | AR-RANGE-MENT (2) | AR-RANGE-MENT (5) | AR-RANGE-MENT (6) | AR-RANGE-MENT (3) | AR-RANGE-MENT (4) | AR-RANGE-MENT (7) |
|---|---|---|---|---|---|---|---|
| FIRST EMBODIMENT | G | B | - | - | R | V | - |
| MODIFICATION EXAMPLE 1-1 | G | B | V | - | R | - | - |
| SECOND EMBODIMENT | G | B | - | - | A | R | - |
| MODIFICATION EXAMPLE 2-1 | G | A | - | - | B | R | - |
| THIRD EMBODIMENT | G | B | - | - | R | IR | - |
| MODIFICATION EXAMPLE 3-1 | G | B | IR | - | R | - | - |
| FOURTH EMBODIMENT | G | B | IR | - | R | V | - |
| MODIFICATION EXAMPLE 4-1 | G | B | V | - | R | IR | - |
| FIFTH EMBODIMENT | G | B | V | - | A | R | - |
| MODIFICATION EXAMPLE 5-1 | G | A | V | - | B | R | - |
| SIXTH EMBODIMENT | G | B | IR | - | A | R | - |
| MODIFICATION EXAMPLE 6-1 | G | A | IR | - | B | R | - |
| SEVENTH EMBODIMENT | G | B | IR | - | A | R | V |
| MODIFICATION EXAMPLE 7-1 | G | A | IR | - | B | R | V |
| MODIFICATION EXAMPLE 7-2 | G | B | V | - | A | R | IR |
| MODIFICATION EXAMPLE 7-3 | G | A | V | - | B | R | IR |
| MODIFICATION EXAMPLE 7-4 | G | B | V | IR | A | R | - |
| MODIFICATION EXAMPLE 7-5 | G | A | V | IR | B | R | - |
| MODIFICATION EXAMPLE 7-6 | G | B | IR | V | A | R | - |
| MODIFICATION EXAMPLE 7-7 | G | A | IR | V | B | R | - |

MEDICAL LIGHT SOURCE DEVICE AND MEDICAL ENDOSCOPIC DEVICE

CROSS-REFERENCE TO RELATED APPLICATION(S)

The present application claims priority to and incorporates by reference the entire contents of Japanese Patent Application No. 2017-208495 filed in Japan on Oct. 27, 2017.

BACKGROUND

The present disclosure relates to a medical light source device and a medical endoscopic device.

In related art, a configuration using a plurality of solid state light emitting elements is known as a medical light source device used in a medical endoscopic device (for example, refer to WO 2015/016172).

In a medical light source device described in WO 2015/016172, a red light emitting diode (LED), a green LED, a blue LED, and a violet LED are adopted as the plurality of solid state light emitting elements. The red LED is disposed such that a center axis of light emitted from the red LED (hereinafter, referred to as R color light) is coincident with a light axis of light emitted from the medical light source device (hereinafter, referred to as an emission light axis). In addition, the green, blue, and violet LEDs are juxtaposed along the emission light axis such that center axes of light emitted from the green LED (hereinafter, referred to as G color light), light emitted from the blue LED (hereinafter, referred to as B color light), and light emitted from the violet LED (hereinafter, referred to as V color light) are respectively orthogonal to the emission light axis, on the same plane including the emission light axis. Then, a dichroic mirror is disposed in each position where the emission light axis intersects with each of the center axes of the G, B, and V color lights.

According to the configuration described above, in the medical light source device described in WO 2015/016172, it is possible to emit the R, G, B, and V color lights.

SUMMARY

However, in the medical light source device described in WO 2015/016172, the green, blue, and violet LEDs are juxtaposed along the emission light axis. For this reason, in the medical light source device, a length dimension in a direction along the emission light axis becomes larger, and thus, it is difficult to reduce the size.

A medical light source device according to one aspect of the present disclosure includes: a first solid state light emitting element configured to emit first color light; a second solid state light emitting element configured to emit second color light of which a peak wavelength is shorter than that of the first color light; a third solid state light emitting element configured to emit third color light of which a peak wavelength is longer than that of the first color light; a fourth solid state light emitting element configured to emit fourth color light of which a peak wavelength is shorter than that of the second color light or is longer than that of the third color light; and a color synthesis optical device configured to synthesize the first color light, the second color light, the third color light, and the fourth color light. The color synthesis optical device includes, a first color separation surface configured to transmit the first color light and the third color light, and reflect the second color light, a second color separation surface disposed to intersect with the first color separation surface, and configured to transmit the first color light and the second color light, and reflect the third color light, and a third color separation surface disposed on a light path latter stage with respect to the first color separation surface and the second color separation surface, and configured to transmit the first color light, the second color light, and the third color light, and reflect the fourth color light.

BRIEF DESCRIPTION OF THE DRAWINGS

FIG. 9 is a diagram illustrating an arrangement pattern of light source units of each of the first to seventh embodiments and Modification Examples 1-1, 2-1, 3-1, 4-1, 5-1, 6-1, and 7-1 to 7-7;

DETAILED DESCRIPTION

Figure 1:
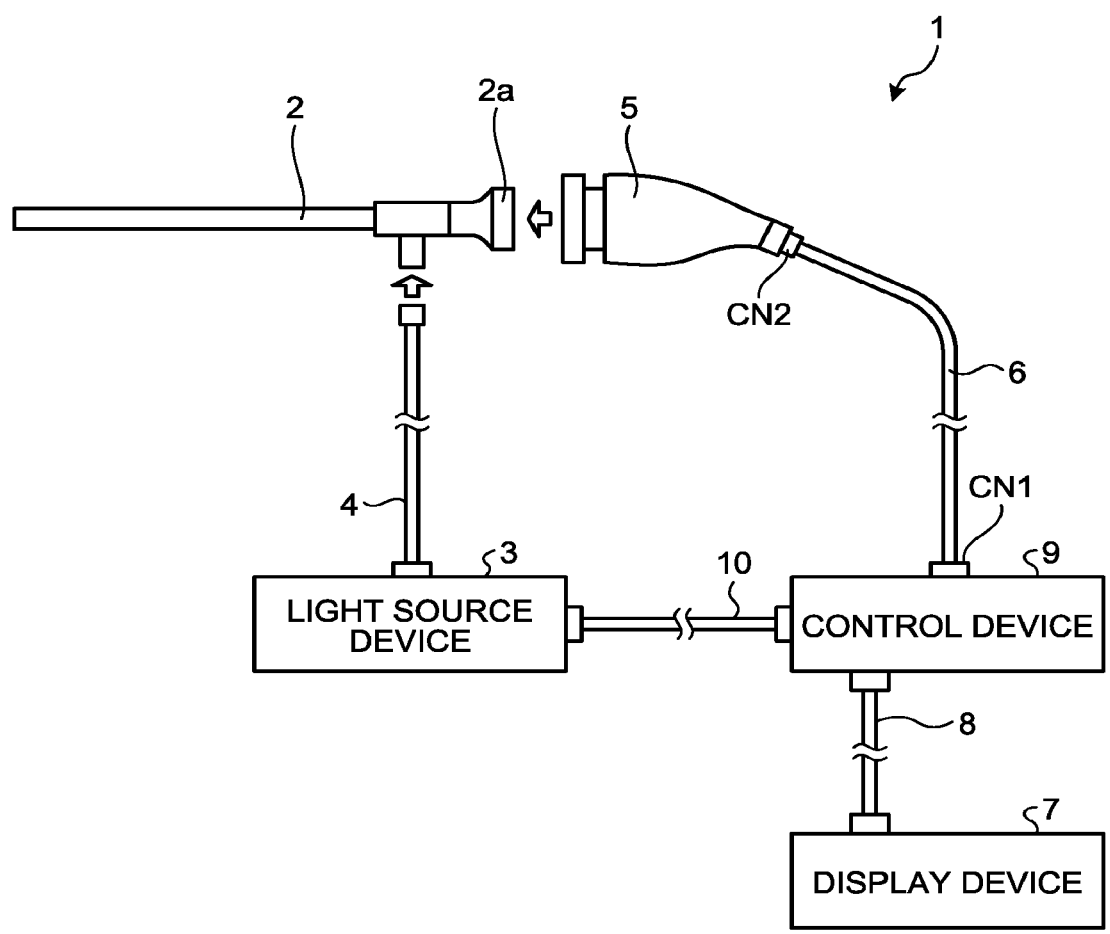
FIG. 1 is a diagram illustrating an outline configuration of a medical endoscopic device according to a first embodiment.

Hereinafter, modes for carrying out the present disclosure (hereinafter, embodiments) will be described with reference to the drawings. Furthermore, the present disclosure is not limited by the embodiments described below. Further, in the drawings, the same reference numerals are applied to the same constituents.

First Embodiment

Outline Configuration of Medical Endoscopic Device

FIG. 1 is a diagram illustrating an outline configuration of a medical endoscopic device 1 according to a first embodiment.

The medical endoscopic device 1 is a device which is used in the medical field, and observes a subject such as the inside of a living body or the like. As illustrated in FIG. 1, the medical endoscopic device 1 includes an insertion portion 2, a light source device 3, a light guide 4, a camera head 5, a first transmission cable 6, a display device 7, a second transmission cable 8, a control device 9, and a third transmission cable 10.

The insertion portion 2 corresponds to an endoscope according to the present disclosure. In the first embodiment, the insertion portion 2 is configured of a rigid endoscope. That is, the insertion portion 2 is rigid or at least a part thereof is flexible, has an elongated shape, and is inserted into the living body. In the insertion portion 2, an optical system which is configured by using one or a plurality of lenses, and condenses a subject image, is disposed.

The light source device 3 corresponds to a medical light source device according to the present disclosure. One end of the light guide 4 is connected to the light source device 3, and the light source device 3 supplies illumination light of illuminating the inside of the living body, to one end of the light guide 4, under the control of the control device 9. Furthermore, the detailed configuration of the light source device 3 will be described below.

One end of the light guide 4 is detachably connected to the light source device 3, and the other end is detachably connected to the insertion portion 2. Then, the light guide 4 transfers light supplied from the light source device 3 from one end to the other end, and supplies the light to the insertion portion 2. The light supplied to the insertion portion 2, is emitted from a distal end of the insertion portion 2, and is emitted into the living body. The light which is emitted into the living body, and is reflected in the living body (the subject image) is condensed by the optical system in the insertion portion 2.

The camera head 5 is detachably connected to a proximal end of the insertion portion 2 (an eyepiece portion 2a (FIG. 1)). Then, the camera head 5 images the subject image condensed in the insertion portion 2, and outputs an image signal (a RAW signal) according to the imaging, under the control of the control device 9. In the first embodiment, the image signal is an image signal of greater than or equal to 4K.

One end of the first transmission cable 6 is detachably connected to the control device 9 through a connector CN1 (FIG. 1), and the other end is detachably connected to the camera head 5 through a connector CN2 (FIG. 1). Then, the first transmission cable 6 transmits the image signal output from the camera head 5 to the control device 9, and transmits a control signal output from the control device 9, a synchronization signal, a clock, power, and the like, to the camera head 5, respectively.

Furthermore, the transmission of the image signal from the camera head 5 to the control device 9 through the first transmission cable 6 may be performed by transmitting the image signal as an optical signal, or may be transmitting the image signal as an electric signal. The same applies to the transmission of the control signal, the synchronization signal, and the clock from the control device 9 to the camera head 5 through the first transmission cable 6.

The display device 7 is configured by using a display using liquid crystal, organic electro luminescence (EL), or the like, and displays an image based on a video signal which is processed in the control device 9.

One end of the second transmission cable 8 is detachably connected to the control device 9, and the other end is detachably connected to the display device 7. Then, the second transmission cable 8 transmits the video signal from the control device 9 to the display device 7.

The control device 9 includes a central processing unit (CPU) or the like, and overall controls the operation of the light source device 3, the camera head 5, and the display device 7.

Specifically, the control device 9 generates the video signal by performing predetermined processing with respect to the image signal acquired from the camera head 5 through the first transmission cable 6, and outputs the video signal to the display device 7 through the second transmission cable 8. Then, the display device 7 displays the image based on the video signal. In addition, the control device 9 outputs the control signal or the like to the camera head 5 or the light source device 3 through the first and third transmission cables 6 and 10.

One end of the third transmission cable 10 is detachably connected to the light source device 3, and the other end is detachably connected to the control device 9. Then, the third transmission cable 10 transmits the control signal from the control device 9 to the light source device 3.

Configuration of Light Source Device

Next, the configuration of the light source device 3 will be described with reference to FIG. 2.

Figure 2:
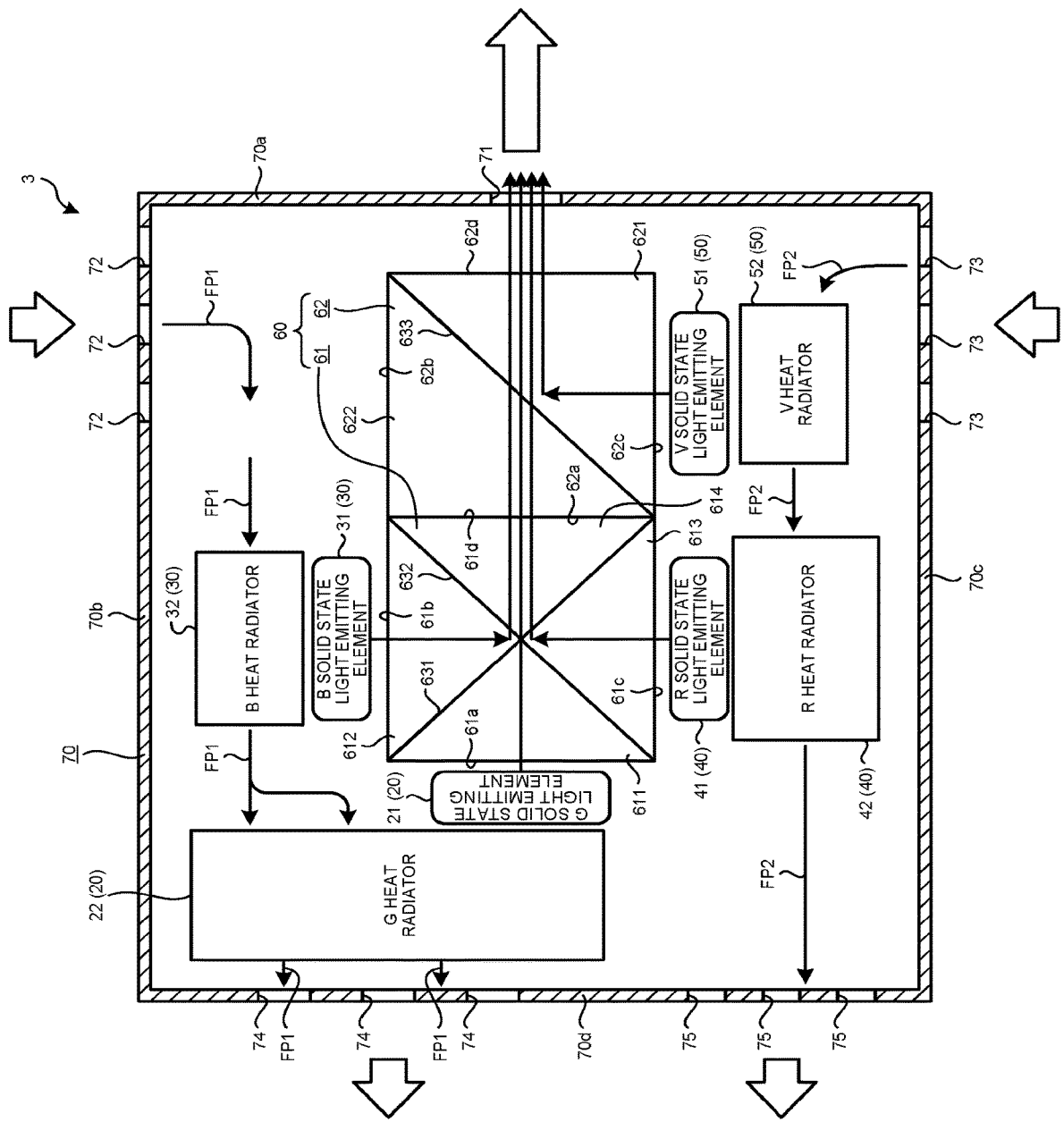
FIG. 2 is a diagram illustrating an internal configuration of the light source device.

FIG. 2 is a diagram illustrating an internal configuration of the light source device 3. Furthermore, FIG. 2 is a diagram in which the internal configuration of the light source device 3 is seen from the upper side.

The light source device 3 includes a G light source unit 20, a B light source unit 30, an R light source unit 40, a V light source unit 50, a color synthesis optical device 60, and an outer casing 70.

The G light source unit 20 is a portion emitting color light having a green wavelength band (hereinafter, referred to as G color light). The G light source unit 20 includes a G solid state light emitting element 21 and a G heat radiator 22.

The G solid state light emitting element 21 corresponds to a first solid state light emitting element according to the present disclosure. In addition, the G color light corresponds to a first color light according to the present disclosure. In the first embodiment, the G solid state light emitting element 21 is configured of a light emitting diode (LED) chip emitting the G color light, and is mounted on a circuit board (not illustrated). Then, the G solid state light emitting element 21 includes a rectangular surface emitting region, and emits the G color light towards a front surface (in FIG. 2, a surface on the right side) side from the surface emitting region.

Here, the G color light, for example, is color light of which a peak wavelength is in a wavelength band range of 495 nm to 590 nm.

The G heat radiator 22 is disposed on a back surface of the circuit board (not illustrated) on which the G solid state light emitting element 21 is mounted (a surface on a side opposite to a mounting surface of the G solid state light emitting element 21), and dissipates heat which is generated at the time of driving the G solid state light emitting element 21, to the outside. In the first embodiment, even though it is not specifically illustrated, the G heat radiator 22 includes a heat spreader, a plurality of fins, and a plurality of heat pipes.

Specifically, the heat spreader is fixed to the back surface of the circuit board (not illustrated) on which the G solid state light emitting element 21 is mounted. The plurality of fins are an approximately flat plate configured of a material having high thermal conductivity, respectively protrude from the heat spreader, and are laminated in a state of having a predetermined gap with each other. One end of the heat pipe is connected to the heat spreader such that heat transfer can be performed, and the other end is connected to each of the plurality of fins through the plurality of fins such that heat transfer can be performed. Accordingly, the heat generated in the G solid state light emitting element 21 is diffused to the heat spreader through the circuit board (not illustrated). In addition, the heat diffused to the heat spreader is transferred to each of the plurality of fins. Further, the heat diffused to the heat spreader is transferred to the other end from one end of each of the plurality of heat pipes, and is transferred to each of the plurality of fins. Then, the heat is dissipated from the plurality of fins, according to thermal exchange between the plurality of fins and the air.

The B light source unit 30 is a portion emitting color light having a blue wavelength band (hereinafter, referred to as B color light). The B light source unit 30 includes a B solid state light emitting element 31 and a B heat radiator 32.

The B solid state light emitting element 31 corresponds to a second solid state light emitting element according to the present disclosure. In addition, the B color light corresponds to a second color light according to the present disclosure. In the first embodiment, the B solid state light emitting element 31 has the same configuration as that of the G solid state light emitting element 21 except that the B color light but not the G color light is emitted.

Here, the B color light, for example, is color light of which a peak wavelength is in a wavelength band range of 450 nm to 495 nm.

The B heat radiator 32 is disposed on the back surface of the circuit board (not illustrated) on which the B solid state light emitting element 31 is mounted, and dissipates heat which is generated at the time of driving the B solid state light emitting element 31, to the outside. In the first embodiment, the B heat radiator 32 has the same configuration as that of the G heat radiator 22.

The R light source unit 40 is a portion emitting color light having a red wavelength band (hereinafter, referred to as R color light). The R light source unit 40 includes an R solid state light emitting element 41 and an R heat radiator 42.

The R solid state light emitting element 41 corresponds to a third solid state light emitting element according to the present disclosure. In addition, the R color light corresponds to a third color light according to the present disclosure. In the first embodiment, the R solid state light emitting element 41 has the same configuration as that of the G solid state light emitting element 21 except that the R color light but not the G color light is emitted.

Here, the R color light, for example, is color light of which a peak wavelength is in a wavelength band range of 620 nm to 750 nm.

The R heat radiator 42 is disposed on the back surface of the circuit board (not illustrated) on which the R solid state light emitting element 41 is mounted, and dissipates heat which is generated at the time of driving the R solid state light emitting element 41, to the outside. In the first embodiment, the R heat radiator 42 has the same configuration as that of the G heat radiator 22.

The V light source unit 50 is a portion emitting color light having a violet wavelength band (hereinafter, referred to as V color light). The V light source unit 50 includes a V solid state light emitting element 51 and a V heat radiator 52.

The V solid state light emitting element 51 corresponds to a fourth solid state light emitting element according to the present disclosure. In addition, the V color light corresponds to fourth color light according to the present disclosure. In the first embodiment, the V solid state light emitting element 51 has the same configuration as that of the G solid state light emitting element 21 except that the V color light but not G color light is emitted.

Here, the V color light, for example, is color light of which a peak wavelength is in a wavelength band range of 380 nm to 450 nm.

The V heat radiator 52 is disposed on the back surface of the circuit board (not illustrated) on which the V solid state light emitting element 51 is mounted, and dissipates heat which is generated at the time of driving the V solid state light emitting element 51, to the outside. In the first embodiment, the V heat radiator 52 has the same configuration as that of the G heat radiator 22.

The color synthesis optical device 60 is capable of synthesizing the G, B, R, and V color lights respectively emitted from the G, B, R, and V solid state light emitting elements 21, 31, 41, and 51. The color synthesis optical device 60 includes first and second prisms 61 and 62.

The first prism 61 is approximately in the shape of a square in the plan view, in which four right angle prisms 611 to 614 are bonded together. Furthermore, hereinafter, in the first prism 61, in four sides of an approximately square in the plan view, an outer surface corresponding to one side will be referred to as a first incidence surface 61a, outer surfaces corresponding to two sides parallel to each other, except for the first incidence surface 61a, will be respectively referred to as second and third incidence surfaces 61b and 61c, and an outer surface corresponding to the other one side will be referred to as a first emission surface 61d.

Then, the G solid state light emitting element 21 is arranged such that a front surface side faces the first incidence surface 61a through an optical system (not illustrated) such as a collimating lens provided between the first incidence surface 61a and the G solid state light emitting element 21. In addition, the B solid state light emitting element 31 is arranged such that a front surface side faces the second incidence surface 61b through the optical system (not illustrated) such as a collimating lens provided between the second incidence surface 61b and the B solid state light emitting element 31. Further, the R solid state light emitting element 41 is arranged such that a front surface side faces the third incidence surface 61c through the optical system (not illustrated) such as a collimating lens provided between the third incidence surface 61c and the R solid state light emitting element 41.

In addition, first and second dielectric multi-layers 631 and 632 are respectively formed on each X-shaped interface in the plan view, in which the right angle prisms 611 to 614 are bonded together.

The first dielectric multi-layer 631 corresponds to a first color separation surface according to the present disclosure. The first dielectric multi-layer 631 is formed on an interface across the first incidence surface 61a and the third incidence surface 61c, in each of the X-shaped interfaces in the plan view, in which the right angle prisms 611 to 614 are bonded together. In the first embodiment, the first dielectric multi-layer 631 is configured of a dielectric multi-layer (a highpass filter) which transmits light having a wavelength of greater than 495 nm, and reflects light having a wavelength of less than or equal to 495 nm.

The second dielectric multi-layer 632 corresponds to second color separation surface according to the present disclosure. The second dielectric multi-layer 632 is formed on an interface across the first incidence surface 61a and the second incidence surface 61b, in each of the X-shaped interfaces in the plan view, in which the right angle prisms 611 to 614 are bonded together. In the first embodiment, the second dielectric multi-layer 632 is configured of a dielectric multi-layer (a lowpass filter) which transmits light having a wavelength of less than 620 nm, and reflects light having a wavelength of greater than or equal to 620 nm.

Then, the G color light emitted from the G solid state light emitting element 21, is incident on the first prism 61 from the first incidence surface 61a, is transmitted through the first and second dielectric multi-layers 631 and 632, and is emitted from the first emission surface 61d. In addition, the B color light emitted from the B solid state light emitting element 31, is incident on the first prism 61 from the second incidence surface 61*b*, is reflected on the first dielectric multi-layer 631 while being transmitted through the second dielectric multi-layer 632, and is emitted from the first emission surface 61*d* by changing a traveling direction by approximately 90°. Further, the R color light emitted from the R solid state light emitting element 41, is incident on the first prism 61 from the third incidence surface 61*c*, is reflected on the second dielectric multi-layer 632 while being transmitted through the first dielectric multi-layer 631, and is emitted from the first emission surface 61*d* by changing the traveling direction by approximately 90°.

The second prism 62 is approximately in the shape of a square in the plan view, in which two right angle prisms 621 and 622 are bonded together. Here, a planar shape of the second prism 62 is set to be identical to a planar shape of the first prism 61. Then, the second prism 62 is arranged such that an outer surface corresponding to one side in four sides of an approximately square in the plan view, abuts on the first emission surface 61*d*, and is in the shape of a rectangle in the plan view, which extends in a right and left direction, along with the first prism 61, in FIG. 2. In addition, the second prism 62 is arranged such that an interface in which the right angle prisms 621 and 622 are bonded together, is parallel to the second dielectric multi-layer 632. Furthermore, hereinafter, in the second prism 62, an outer surface abutting on the first emission surface 61*d* will be referred to as an abutting surface 62*a*, an outer surface obtained by extending the second incidence surface 61*b* will be referred to as a fourth incidence surface 62*b*, an outer surface obtained by extending the third incidence surface 61*c* will be referred to as a fifth incidence surface 62*c*, and an outer surface to be parallel to the abutting surface 62*a* will be referred to as a second emission surface 62*d*.

Then, the V solid state light emitting element 51 is arranged such that a front surface side faces the fifth incidence surface 62*c* through the optical system (not illustrated) such as a collimating lens provided between the fifth incidence surface 62*c* and the V solid state light emitting element 51.

In addition, a third dielectric multi-layer 633 is formed on the interface in which the right angle prisms 621 and 622 are bonded together.

The third dielectric multi-layer 633 corresponds to a third color separation surface according to the present disclosure. In the first embodiment, the third dielectric multi-layer 633 is configured of a dielectric multi-layer (a highpass filter) which transmits light having a wavelength of greater than 450 nm, and reflects light having a wavelength of less than or equal to 450 nm.

Then, the G, B, and R color lights emitted from the first emission surface 61*d*, are incident on the second prism 62 from the abutting surface 62*a*, are transmitted through the third dielectric multi-layer 633, and are emitted from the second emission surface 62*d*. In addition, the V color light emitted from the V solid state light emitting element 51, is incident on the second prism 62 from the fifth incidence surface 62*c*, is reflected on the third dielectric multi-layer 633, and is emitted from the second emission surface 62*d* by changing the traveling direction by approximately 90°.

As described above, the color synthesis optical device 60 is capable of synthesizing the G, B, R, and V color lights.

Here, in the first embodiment, the light source device 3 is operated in two operation modes of a white light mode and a narrow band imaging (NBI) mode described below, under the control of the control device 9.

In the white light mode, only the G, B, and R solid state light emitting elements 21, 31, and 41 are driven. Then, the light source device 3 (the color synthesis optical device 60) synthesizes G, B, and R color lights, and emits white light.

In the NBI mode, only the B and V solid state light emitting elements 31 and 51 are driven. Then, the light source device 3 (the color synthesis optical device 60) synthesizes the B and V color lights to be emitted.

The outer casing 70 is approximately in the shape of a rectangular parallelepiped as a whole, and the G, B, R, and V light source units 20, 30, 40, and 50 and the color synthesis optical device 60 are contained in the outer casing 70. Furthermore, hereinafter, in the outer casing 70, in four side walls excluding a top surface and a bottom surface, a side wall on the second emission surface 62*d* side will be referred to as a front portion 70*a*, a side wall on the second incidence surface 61*b* side will be referred to as a first side wall portion 70*b*, a side wall on the third incidence surface 61*c* and the fifth incidence surface 62*c* sides will be referred to as a second side wall portion 70*c*, and a side wall on the first incidence surface 61*a* side will be referred to as a back portion 70*d*.

In the front portion 70*a*, an emission hole 71 to which one end of the light guide 4 is connected, is formed in a position facing the second emission surface 62*d*. Then, the light emitted from the second emission surface 62*d*, is supplied to one end of the light guide 4 through the optical system (not illustrated) and the emission hole 71.

In the first side wall portion 70*b*, a first intake hole 72 for taking in cooling air on the outside of the outer casing 70, is formed in a position on the front portion 70*a* side.

Similarly, in the second side wall portion 70*c*, a second intake hole 73 for taking in the air on the outside of the outer casing 70, is formed in a position on the front portion 70*a* side.

Here, the first and second intake holes 72 and 73 correspond to an intake hole according to the present disclosure.

In the back portion 70*d*, a first exhaust hole 74 for discharging the air in the outer casing 70 to the outside, is formed in a position on the first side wall portion 70*b* side.

Similarly, in the back portion 70*d*, a second exhaust hole 75 for discharging the air in the outer casing 70 to the outside, is formed in a position on the second side wall portion 70*c* side.

In addition, in the outer casing 70, a plurality of cooling fans (not illustrated) are disposed, and first and second cooling flow paths FP1 and FP2 respectively circulating the cooling air according to the driving of the plurality of cooling fans are disposed. Furthermore, the first and second cooling flow paths FP1 and FP2 are flow paths which are independent from each other by a current plate (not illustrated) or the like.

The first cooling flow path FP1 is a flow path from the first intake hole 72 to the first exhaust hole 74. In the first cooling flow path FP1, G and B heat radiators 22 and 32 are disposed. That is, the air taken in the outer casing 70 through the first intake hole 72 according to the driving of the cooling fan (not illustrated), is circulated by following the first cooling flow path FP1, and thus, cools the B heat radiator 32 and the G heat radiator 22, and is discharged to the outside of the outer casing 70 through the first exhaust hole 74.

The second cooling flow path FP2 is a flow path from the second intake hole 73 to the second exhaust hole 75. In the second cooling flow path FP, R and V heat radiators 42 and 52 are disposed. That is, the air taken in the outer casing 70 through the second intake hole 73 according to the driving of the cooling fan (not illustrated), is circulated by following the second cooling flow path FP2, and thus, cools the V heat radiator 52 and the R heat radiator 42, and is discharged to the outside of the outer casing 70 through the second exhaust hole 75.

That is, a part of the first and second cooling flow paths FP1 and FP2 are disposed to be parallel to a center axis of the G color light on each of one side and the other side sandwiching the color synthesis optical device 60.

According to the first embodiment described above, the following effects are obtained.

In the light source device 3 according to the first embodiment, the color synthesis optical device 60 capable of synthesizing the G, B, R, and V color lights respectively emitted from the G, B, R, and V solid state light emitting elements 21, 31, 41, and 51, is provided. The color synthesis optical device 60 includes the first and second dielectric multi-layers 631 and 632 which are disposed to intersect with each other, and the third dielectric multi-layer 633 which is disposed on the light path latter stage of the first and second dielectric multi-layers 631 and 632. That is, the first and second dielectric multi-layers 631 and 632 are disposed to intersect with each other, and thus, it is not necessary to juxtapose the B and R solid state light emitting elements 31 and 41 along a light axis of the light emitted from the light source device 3 (in FIG. 2, a light axis along the right and left direction (hereinafter, referred to as an emission light axis)), and it is possible to dispose the B and R solid state light emitting elements 31 and 41 in approximately the same position in a direction along the emission light axis.

Therefore, according to the light source device 3 of the first embodiment, it is possible to decrease a length dimension in the direction along the emission light axis, and to reduce the size.

In addition, according to the light source device 3 of the first embodiment, the G, B, R, and V light source units 20, 30, 40, and 50 are disposed as described above, and thus, the first to third dielectric multi-layer 631 to 633 can be configured of a highpass filter or a lowpass filter, which is inexpensive, but not a bandpass filter.

In addition, in the light source device 3 according to the first embodiment, in the outer casing 70, the first and second cooling flow paths FP1 and FP2, which are independent from each other, are respectively disposed. Then, the G solid state light emitting element 21 is cooled by the cooling air circulated through the first cooling flow path FP1. The R solid state light emitting element 41 is cooled by the cooling air circulated through the second cooling flow path FP2. For this reason, it is possible to separately cool the G and R solid state light emitting elements 21 and 41 having a comparatively large calorific value, by using the first and second cooling flow paths FP1 and FP2 independent from each other, and to efficiently cool the G and R solid state light emitting elements 21 and 41.

In addition, in the light source device 3 according to the first embodiment, the B solid state light emitting element 31 is cooled by the cooling air circulated through the first cooling flow path FP1. In addition, the B solid state light emitting element 31 and the R solid state light emitting element 41 are disposed on each of one side and the other side sandwiching the color synthesis optical device 60. Further, a part of the first and second cooling flow paths FP1 and FP2 are disposed to be parallel to the center axis of the G color light, on each of one side and the other side sandwiching the color synthesis optical device 60. For this reason, the B solid state light emitting element 31 which is separated from the R solid state light emitting element 41, and is close to the G solid state light emitting element 21, can be cooled by using the first cooling flow path FP1 which is identical to the G solid state light emitting element 21, and the cooling flow path disposed in the outer casing 70 is not complicated.

In addition, in the light source device 3 according to the first embodiment, the first and second intake holes 72 and 73, and the first and second exhaust holes 74 and 75 are respectively disposed on different side walls in the outer casing 70. For this reason, the air discharged from the first and second exhaust holes 74 and 75 (the air warmed in the outer casing 70) is not taken in from the first and second intake holes 72 and 73. That is, it is possible to constantly circulate fresh air (air having a comparatively low temperature) to the first and second cooling flow paths FP1 and FP2 through the first and second intake holes 72 and 73, and to effectively cool the G, B, R, and V solid state light emitting elements 21, 31, 41, and 51.

In addition, in the light source device 3 according to the first embodiment, the color synthesis optical device 60 is a dichroic prism in which a plurality of prisms 611 to 614, and 621 and 622 are integrally incorporated. For this reason, it is possible to easily realize a structure in which the first and second dielectric multi-layers 631 and 632 intersect with each other.

Modification Example 1-1 of First Embodiment

In the first embodiment described above, the V light source unit 50 (the V solid state light emitting element 51) is disposed to face the fifth incidence surface 62c, but is not limited thereto, and may be disposed to face the fourth incidence surface 62b. At this time, the third dielectric multi-layer 633 is disposed to be parallel to the first dielectric multi-layer 631. Then, in the configuration, in the first cooling flow path FP1, the G, B, and V heat radiators 22, 32, and 52 are disposed. In addition, in the second cooling flow path FP2, only the R heat radiator 42 is disposed.

Second Embodiment

Next, a second embodiment of the present disclosure will be described.

In the following description, the same reference numerals will be applied to the same configurations as those of the first embodiment described above, and the detailed description will be omitted or simplified.

Figure 3:
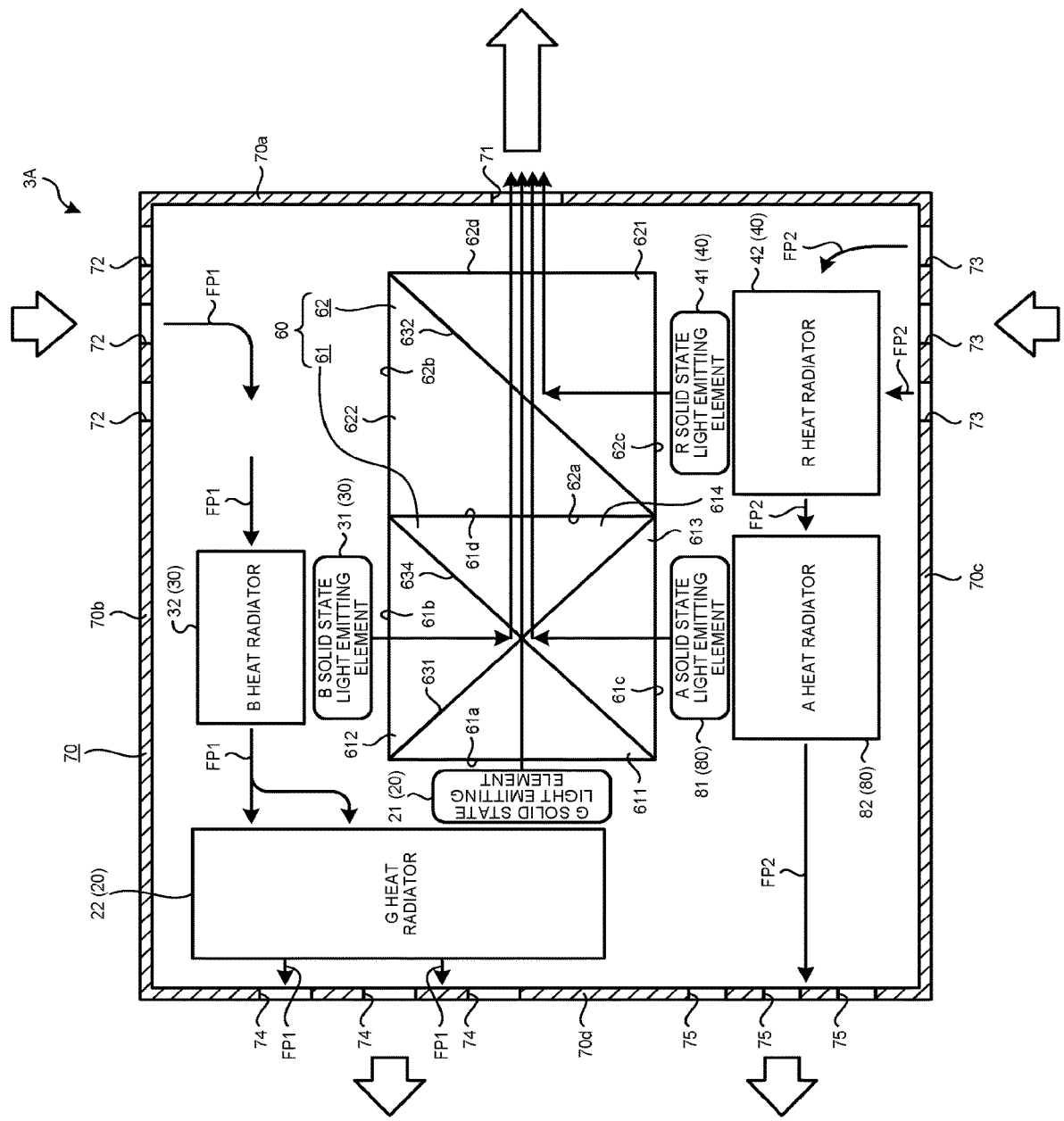
FIG. 3 is a diagram illustrating an internal configuration of a light source device according to a second embodiment.

FIG. 3 is a diagram illustrating an internal configuration of a light source device 3A according to the second embodiment.

In the second embodiment, as illustrated in FIG. 3, the light source device 3A is adopted instead of the light source device 3 (FIG. 2) in the first embodiment described above. Furthermore, the light source device 3A corresponds to the medical light source device according to the present disclosure.

Hereinafter, the configuration of the light source device 3A will be described with reference to FIG. 3.

In the light source device 3A, an A light source unit 80 is disposed in a disposing position of the R light source unit 40, with respect to the light source device 3 in the first embodiment described above.

The A light source unit 80 is a portion emitting color light having an orange wavelength band (hereinafter, referred to as A color light). The A light source unit 80 includes an A solid state light emitting element 81 and an A heat radiator 82.

The A solid state light emitting element 81 corresponds to the third solid state light emitting element according to the present disclosure. In addition, the A color light corresponds to the third color light according to the present disclosure. In the second embodiment, the A solid state light emitting element 81 has the same configuration as that of the G solid state light emitting element 21 except that the A color light but not the G color light is emitted.

Here, the A color light, for example, is color light of which a peak wavelength is in a wavelength band range of 590 nm to 620 nm.

Then, the A solid state light emitting element 81 is arranged such that a front surface side faces the third incidence surface 61c through the optical system (not illustrated) such as a collimating lens provided between the third incidence surface 61c and the A solid state light emitting element 81.

The A heat radiator 82 is disposed on the back surface of the circuit board (not illustrated) on which the A solid state light emitting element 81 is mounted, and dissipates heat which is generated at the time of driving the A solid state light emitting element 81, to the outside. In the second embodiment, the A heat radiator 82 has the same configuration as that of the G heat radiator 22.

In addition, in the light source device 3A, the R light source unit 40 is disposed in a disposing position of the V light source unit 50, with respect to the light source device 3 in the first embodiment described above.

Here, the R solid state light emitting element 41 is arranged such that a front surface side faces the fifth incidence surface 62c through the optical system (not illustrated) such as a collimating lens provided between the fifth incidence surface 62c and the R solid state light emitting element 41. In the second embodiment, the R solid state light emitting element 41 corresponds to the fourth solid state light emitting element according to the present disclosure. In addition, the R color light corresponds to the fourth color light.

That is, in the second embodiment, in the second cooling flow path FP2, the R and A heat radiators 42 and 82 are disposed.

In addition, in the light source device 3A, the A solid state light emitting element 81 is disposed to face the third incidence surface 61c, and thus, a fourth dielectric multi-layer 634 is adopted instead of the second dielectric multi-layer 632, with respect to the light source device 3 in the first embodiment described above.

The fourth dielectric multi-layer 634 corresponds to the second color separation surface according to the present disclosure. In the second embodiment, the fourth dielectric multi-layer 634 is configured of a dielectric multi-layer (a lowpass filter) which transmits light having a wavelength of less than 590 nm, and reflects light having a wavelength of greater than or equal to 590 nm.

Then, the G color light emitted from the G solid state light emitting element 21, is incident on the first prism 61 from the first incidence surface 61a, is transmitted through the first and fourth dielectric multi-layers 631 and 634, and is emitted from the first emission surface 61d. In addition, the B color light emitted from the B solid state light emitting element 31, is incident on the first prism 61 from the second incidence surface 61b, is reflected on the first dielectric multi-layer 631 while being transmitted through the fourth dielectric multi-layer 634, and is emitted from the first emission surface 61d by changing the traveling direction by approximately 90°. Further, the A color light emitted from the A solid state light emitting element 81, is incident on the first prism 61 from the third incidence surface 61c, is reflected on the fourth dielectric multi-layer 634 while being transmitted through the first dielectric multi-layer 631, and is emitted from the first emission surface 61d by changing the traveling direction by approximately 90°.

Further, in the light source device 3A, the R solid state light emitting element 41 is disposed to face the fifth incidence surface 62c, and thus, a second dielectric multi-layer 632 is adopted instead of the third dielectric multi-layer 633, with respect to the light source device 3 in the first embodiment described above.

In the second embodiment, the second dielectric multi-layer 632 corresponds to the third color separation surface according to the present disclosure.

Then, the G, B, and A color lights emitted from the first emission surface 61d, are incident on the second prism 62 from the abutting surface 62a, are transmitted through the second dielectric multi-layer 632, and are emitted from the second emission surface 62d. In addition, the R color light emitted from the R solid state light emitting element 41, is incident on the second prism 62 from the fifth incidence surface 62c, is reflected on the second dielectric multi-layer 632, and is emitted from the second emission surface 62d by changing the traveling direction by approximately 90°.

As described above, the color synthesis optical device 60 according to the second embodiment is capable of synthesizing the G, B, A, and R color lights. That is, the light source device 3A is capable of supplying the G, B, A, and R color lights to one end of the light guide 4.

Here, in the second embodiment, the light source device 3A is operated in two operation modes of the white light mode in the first embodiment described above and a blood vessel emphasizing mode described below, under the control of the control device 9.

In the blood vessel emphasizing mode, only the G, R, and A solid state light emitting elements 21, 41, and 81 are driven. Then, the light source device 3A (the color synthesis optical device 60) synthesizes the G, R, and A color lights to be emitted.

Even in a case of adopting the light source device 3A according to the second embodiment described above, the same effects as those of the first embodiment described above are obtained.

Modification Example 2-1 of Second Embodiment

In the second embodiment described above, a positional relationship between the B light source unit 30 and the A light source unit 80 may be reversed. At this time, a positional relationship between the first and fourth dielectric multi-layers 631 and 634 is also reversed. Then, in the configuration, in the first cooling flow path FP1, the G and A heat radiators 22 and 82 are disposed. In addition, in the second cooling flow path FP2, the B and R heat radiators 32 and 42 are disposed.

Third Embodiment

Next, a third embodiment of the present disclosure will be described.

In the following description, the same reference numerals will be applied to the same configurations as those of the first embodiment described above, and the detailed description will be omitted or simplified.

Figure 4:
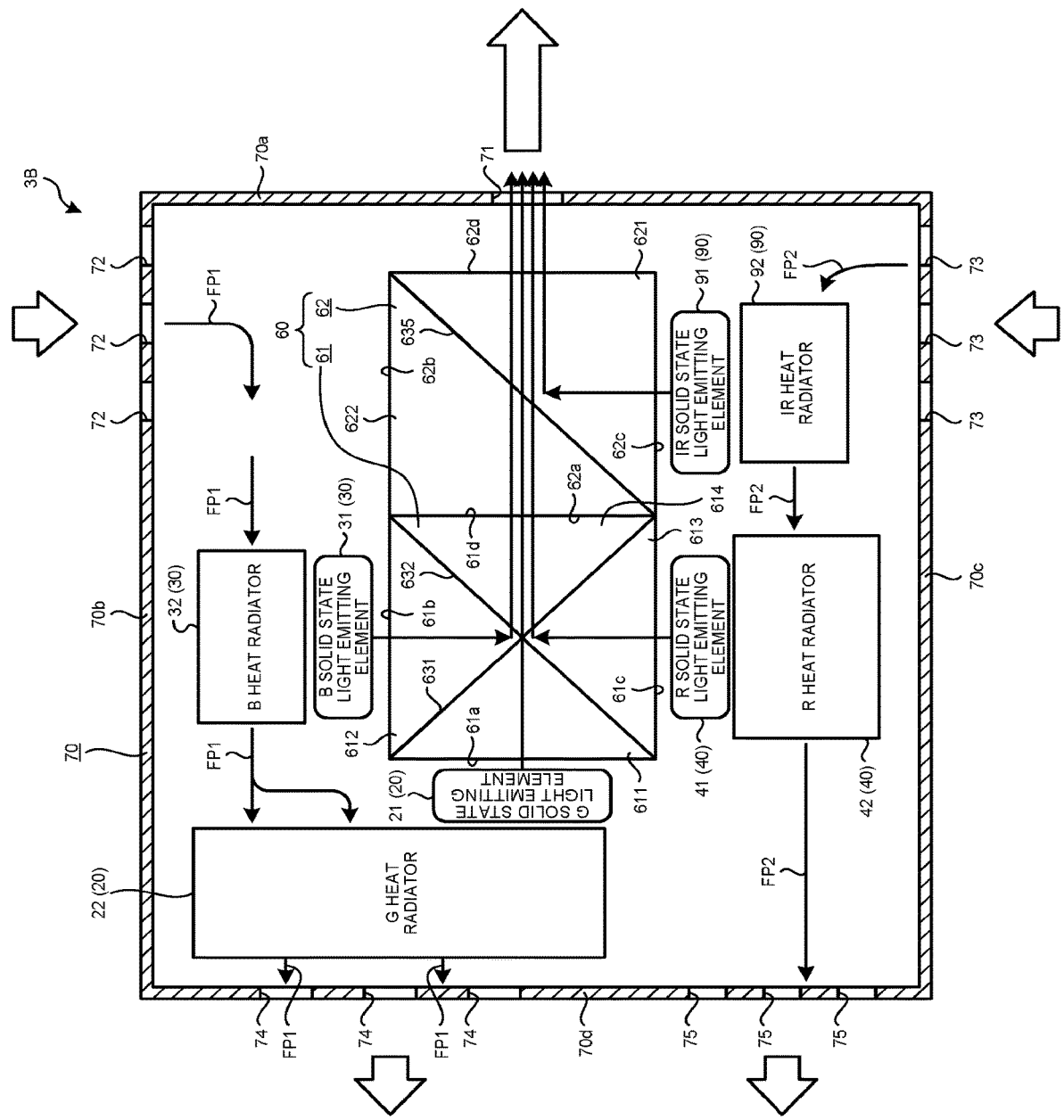
FIG. 4 is a diagram illustrating an internal configuration of a light source device according to a third embodiment.

FIG. 4 is a diagram illustrating an internal configuration of a light source device 3B according to the third embodiment.

In the third embodiment, as illustrated in FIG. 4, the light source device 3B is adopted instead of the light source device 3 (FIG. 2) in the first embodiment described above. Furthermore, the light source device 3B corresponds to the medical light source device according to the present disclosure.

Hereinafter, the configuration of the light source device 3B will be described with reference to FIG. 4.

In the light source device 3B, an IR light source unit 90 is disposed in the disposing position of the V light source unit 50, with respect to the light source device 3 in the first embodiment described above.

The IR light source unit 90 is a portion emitting color light having an infrared wavelength band (hereinafter, referred to as IR color light). The IR light source unit 90 includes an IR solid state light emitting element 91 and an IR heat radiator 92.

The IR solid state light emitting element 91 corresponds to the fourth solid state light emitting element according to the present disclosure. In addition, the IR color light corresponds to the fourth color light according to the present disclosure. In the third embodiment, the IR solid state light emitting element 91 has the same configuration as that of the G solid state light emitting element 21 except that the IR color light but not the G color light is emitted.

Here, the IR color light, for example, is color light of which a peak wavelength is in a wavelength band range of greater than or equal to 750 nm.

Then, the IR solid state light emitting element 91 is arranged such that a front surface side faces the fifth incidence surface 62c through the optical system (not illustrated) such as a collimating lens provided between the fifth incidence surface 62c and the IR solid state light emitting element 91.

The IR heat radiator 92 is disposed on the back surface of the circuit board (not illustrated) on which the IR solid state light emitting element 91 is mounted, and dissipates heat which is generated at the time of driving the IR solid state light emitting element 91, to the outside. In the third embodiment, the IR heat radiator 92 has the same configuration as that of the G heat radiator 22.

That is, in the third embodiment, the R and IR heat radiators 42 and 92 are disposed in the second cooling flow path FP2.

In addition, in the light source device 3B, the IR solid state light emitting element 91 is disposed to face the fifth incidence surface 62c, and thus, a fifth dielectric multi-layer 635 is adopted instead of the third dielectric multi-layer 633, with respect to the light source device 3 in the first embodiment described above.

The fifth dielectric multi-layer 635 corresponds to the third color separation surface according to the present disclosure. In the third embodiment, the fifth dielectric multi-layer 635 is configured of a dielectric multi-layer (a lowpass filter) which transmits light having a wavelength of less than 750 nm, and reflects light having a wavelength of greater than or equal to 750 nm.

Then, the G, B, and R color lights emitted from the first emission surface 61d, are incident on the second prism 62 from the abutting surface 62a, are transmitted through the fifth dielectric multi-layer 635, and are emitted from the second emission surface 62d. In addition, the IR color light emitted from the IR solid state light emitting element 91, is incident on the second prism 62 from the fifth incidence surface 62c, is reflected on the fifth dielectric multi-layer 635, and is emitted from the second emission surface 62d by changing the traveling direction by approximately 90°.

As described above, the color synthesis optical device 60 according to the third embodiment is capable of synthesizing the G, B, R, and IR color lights. That is, the light source device 3B is capable of supplying the G, B, R, and IR color lights to one end of the light guide 4.

Here, in the third embodiment, the light source device 3B is operated in two operation modes of the white light mode in the first embodiment described above, and a fluorescent observation mode described below, under the control of the control device 9.

In the fluorescent observation mode, only the IR solid state light emitting element 91 is driven. Then, the light source device 3 (the color synthesis optical device 60) emits only the IR color light.

Even in a case of adopting the light source device 3B according to the third embodiment described above, the same effects as those of the first embodiment described above are obtained.

Modification Example 3-1 of Third Embodiment

In the third embodiment described above, the IR light source unit 90 (the IR solid state light emitting element 91) is disposed to face the fifth incidence surface 62c, but is not limited thereto, and may be disposed to face the fourth incidence surface 62b. At this time, the fifth dielectric multi-layer 635 is disposed to be parallel to the first dielectric multi-layer 631. Then, in the configuration, the G, B, and IR heat radiators 22, 32, and 92 are disposed in the first cooling flow path FP1. In addition, only the R heat radiator 42 is disposed in the second cooling flow path FP2.

Fourth Embodiment

Next, a fourth embodiment of the present disclosure will be described.

In the following description, the same reference numerals will be applied to the same configurations as those of the first embodiment described above, and the detailed description will be omitted or simplified.

Figure 5:
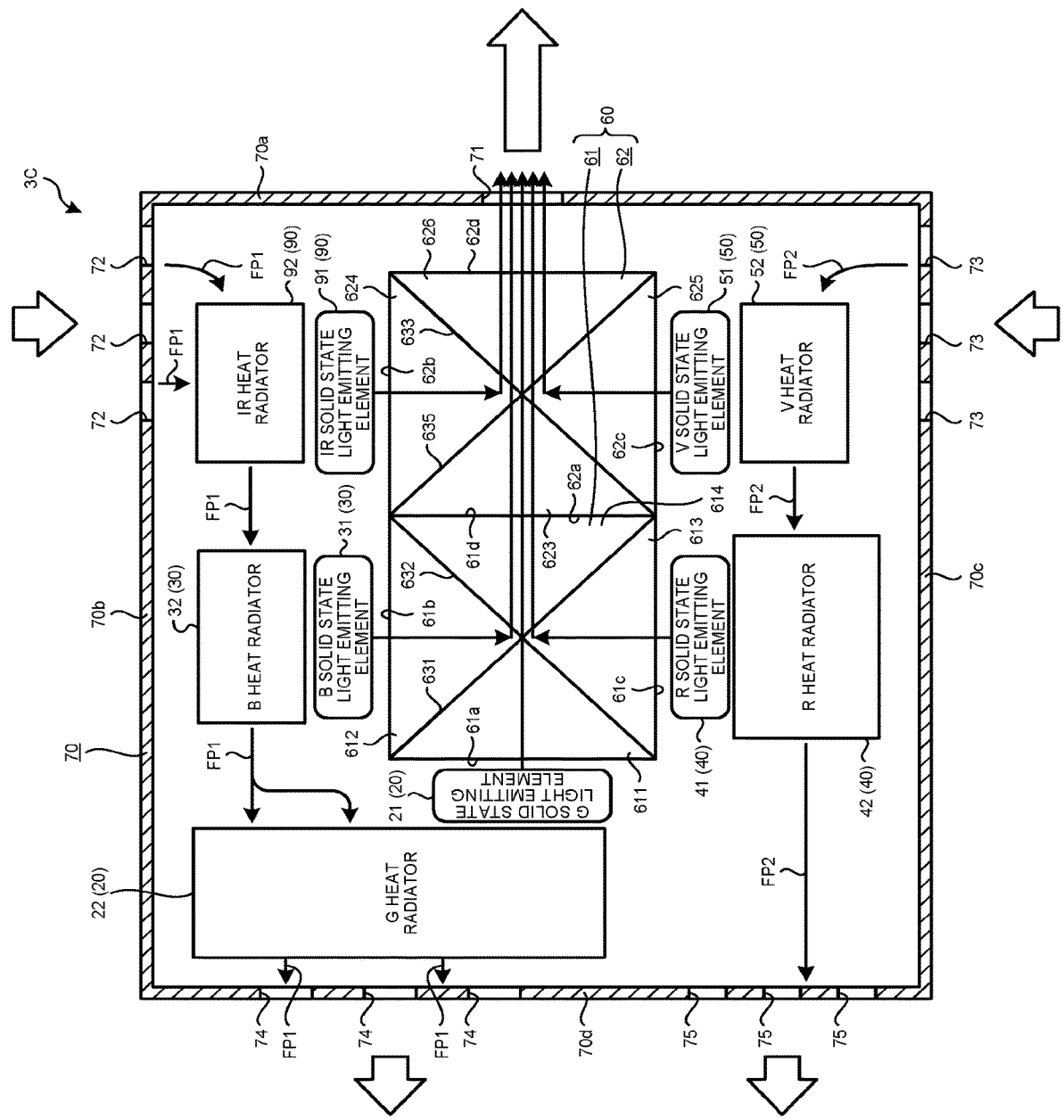
FIG. 5 is a diagram illustrating an internal configuration of a light source device according to a fourth embodiment.

FIG. 5 is a diagram illustrating an internal configuration of a light source device 3C according to the fourth embodiment.

In the fourth embodiment, as illustrated in FIG. 5, the light source device 3C is adopted instead of the light source device 3 (FIG. 2) in the first embodiment described above. Furthermore, the light source device 3C corresponds to the medical light source device according to the present disclosure.

Hereinafter, the configuration of the light source device 3C will be described with reference to FIG. 5.

In the light source device 3C, the IR light source unit 90 in the third embodiment described above is added, with respect to the light source device 3 in the first embodiment described above.

Here, the IR solid state light emitting element 91 is arranged such that a front surface side faces the fourth incidence surface 62b through the optical system (not illustrated) such as a collimating lens provided between the fourth incidence surface 62b and the IR solid state light emitting element 91. Furthermore, in the fourth embodiment, the IR solid state light emitting element 91 corresponds to the fourth solid state light emitting element according to the present disclosure. In addition, the IR color light corresponds to the fourth color light according to the present disclosure. Further, the V solid state light emitting element 51 corresponds to a fifth solid state light emitting element according to the present disclosure. In addition, the V color light corresponds to fifth color light according to the present disclosure.

That is, in the fourth embodiment, the G, B, and IR heat radiators 22, 32, and 92 are disposed in the first cooling flow path FP1.

In addition, in the light source device 3A, the IR solid state light emitting element 91 is disposed to face the fourth incidence surface 62b, and thus, the second prism 62 is configured of four right angle prisms 623 to 626, as with the first prism 61, with respect to the light source device 3 in the first embodiment described above.

Here, the fifth dielectric multi-layer 635 is formed on an interface across the abutting surface 62a and the fifth incidence surface 62c (an interface parallel to the first dielectric multi-layer 631), in each of X-shaped interfaces in the plan view in which the right angle prisms 623 to 626 are bonded together. On the other hand, the third dielectric multi-layer 633 is formed on an interface across the abutting surface 62a and the fourth incidence surface 62b (an interface parallel to the second dielectric multi-layer 632). Furthermore, in the fourth embodiment, the fifth dielectric multi-layer 635 corresponds to the third color separation surface according to the present disclosure. In addition, the third dielectric multi-layer 633 corresponds to a fourth color separation surface according to the present disclosure.

Then, the G, B, and R color lights emitted from the first emission surface 61d, are incident on the second prism 62 from the abutting surface 62a, are transmitted through the third and fifth dielectric multi-layers 633 and 635, and are emitted from the second emission surface 62d. In addition, the IR color light emitted from the IR solid state light emitting element 91, is incident on the second prism 62 from the fourth incidence surface 62b, is reflected on the fifth dielectric multi-layer 635 while being transmitted through the third dielectric multi-layer 633, and is emitted from the second emission surface 62d by changing the traveling direction by approximately 90°. Further, the V color light emitted from the V solid state light emitting element 51, is incident on the second prism 62 from the fifth incidence surface 62c, is reflected on the third dielectric multi-layer 633 while being transmitted through the fifth dielectric multi-layer 635, and is emitted from the second emission surface 62d by changing the traveling direction by approximately 90°.

As described above, the color synthesis optical device 60 according to the fourth embodiment is capable of synthesizing the G, B, R, V, and IR color lights. That is, the light source device 3C is capable of supplying the G, B, R, V, and IR color lights to one end of the light guide 4.

Here, in the fourth embodiment, the light source device 3C is operated in three operation modes of the white light mode and the NBI mode in the first embodiment described above, and the fluorescent observation mode in the third embodiment described above, under the control of the control device 9.

According to the fourth embodiment described above, the following effects are obtained, in addition to the same effects as those of the first embodiment described above.

In the light source device 3C according to the fourth embodiment, the color synthesis optical device 60 capable of synthesizing the G, B, R, V, and IR color lights respectively emitted from the G, B, R, V, and IR solid state light emitting elements 21, 31, 41, 51, and 91, is provided. The color synthesis optical device 60 includes the first and second dielectric multi-layers 631 and 632 which are disposed to intersect with each other, and the third and fifth dielectric multi-layers 633 and 635 which are disposed on the light path latter stage of the first and second dielectric multi-layers 631 and 632, and are disposed to intersect with each other. That is, the third and fifth dielectric multi-layers 633 and 635 are disposed to intersect with each other, and thus, it is not necessary to juxtapose the V and IR solid state light emitting elements 51 and 91 along the emission light axis, and it is possible to dispose the V and IR solid state light emitting elements 51 and 91 in approximately the same position in the direction along the emission light axis.

Therefore, according to light source device 3C of the fourth embodiment, even in a case of adopting five solid state light emitting elements of the G, B, R, B, and IR solid state light emitting elements 21, 31, 41, 51, and 91, it is possible to decrease the length dimension in the direction along the emission light axis, and to reduce the size.

Modification Example 4-1 of Fourth Embodiment

In the fourth embodiment described above, a positional relationship between the V light source unit 50 and the IR light source unit 90 may be reversed. At this time, a positional relationship between the third and fifth dielectric multi-layers 633 and 635 is also reversed. Then, in the configuration, the G, B, and V heat radiators 22, 32, and 52 are disposed in the first cooling flow path FP1. In addition, the R and IR heat radiators 42 and 92 are disposed in the second cooling flow path FP2.

Fifth Embodiment

Next, a fifth embodiment of the present disclosure will be described.

In the following description, the same reference numerals will be applied to the same configurations as those of the first embodiment described above, and the detailed description will be omitted or simplified.

Figure 6:
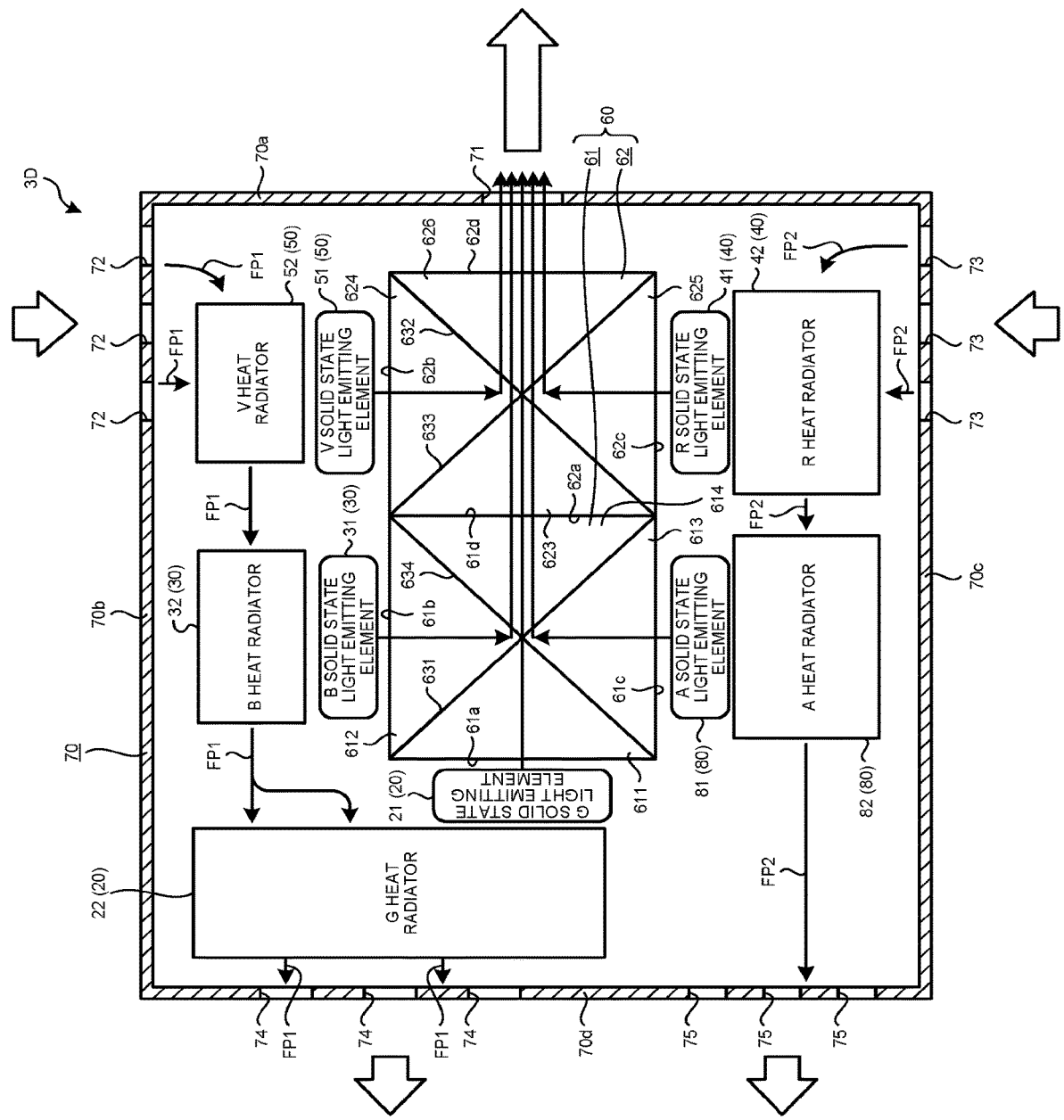
FIG. 6 is a diagram illustrating an internal configuration of a light source device according to a fifth embodiment.

FIG. 6 is a diagram illustrating an internal configuration of a light source device 3D according to the fifth embodiment.

In the fifth embodiment, as illustrated in FIG. 6, the light source device 3D is adopted instead of the light source device 3 (FIG. 2) in the first embodiment described above. Furthermore, the light source device 3D corresponds to the medical light source device according to the present disclosure.

Hereinafter, the configuration of the light source device 3D will be described with reference to FIG. 6.

In the light source device 3D, as with the second embodiment described above, the A light source unit 80 is disposed in the disposing position of the R light source unit 40, and the R light source unit 40 is disposed in the disposing position of the V light source unit 50, with respect to the light source device 3 in the first embodiment described above. In the fifth embodiment, the A solid state light emitting element 81 corresponds to the third solid state light emitting element according to the present disclosure. In addition, the A color light corresponds to the third color light according to the present disclosure. Further, the R solid state light emitting element 41 corresponds to the fourth solid state light emitting element according to the present disclosure. In addition, the R color light corresponds to the fourth color light according to the present disclosure.

That is, in the fifth embodiment, as with the second embodiment described above, the R and A heat radiators 42 and 82 are disposed in the second cooling flow path FP2.

In addition, in the light source device 3D, the V light source unit 50 is disposed in a position facing the fourth incidence surface 62b, with respect to the light source device 3 in the first embodiment described above.

Here, the V solid state light emitting element 51 is disposed such that a front surface side faces the fourth incidence surface 62b through the optical system (not illustrated) such as a collimating lens provided between the fourth incidence surface 62b and the V solid state light emitting element 51. In the fifth embodiment, the V solid state light emitting element 51 corresponds to the fifth solid state light emitting element according to the present disclosure. In addition, the V color light corresponds to the fifth color light according to the present disclosure.

That is, in the fifth embodiment, the G, B, and V heat radiators 22, 32, and 52 are disposed in the first cooling flow path FP1.

In addition, in the light source device 3D, the V solid state light emitting element 51 is disposed to face the fourth incidence surface 62b, and the R solid state light emitting element 41 is disposed to face the fifth incidence surface 62c, and thus, as with the fourth embodiment described above, the second prism 62 is configured of four right angle prisms 623 to 626, with respect to the light source device 3 in the first embodiment described above.

In the second prism 62 according to the fifth embodiment, the third dielectric multi-layer 633 is adopted instead of the fifth dielectric multi-layer 635, and the second dielectric multi-layer 632 is adopted instead of the third dielectric multi-layer 633, with respect to the second prism 62 in the fourth embodiment described above. In the fifth embodiment, the second dielectric multi-layer 632 corresponds to the third color separation surface according to the present disclosure. In addition, the third dielectric multi-layer 633 corresponds to the fourth color separation surface according to the present disclosure.

Then, the G, B, and A color lights emitted from the first emission surface 61d, are incident on the second prism 62 from the abutting surface 62a, are transmitted through the second and third dielectric multi-layers 632 and 633, and are emitted from the second emission surface 62d. In addition, the V color light emitted from the V solid state light emitting element 51, is incident on the second prism 62 from the fourth incidence surface 62b, is reflected on the third dielectric multi-layer 633 while being transmitted through the second dielectric multi-layer 632, and is emitted from the second emission surface 62d by changing the traveling direction by approximately 90°. Further, the R color light emitted from the R solid state light emitting element 41, is incident on the second prism 62 from the fifth incidence surface 62c, is reflected on the second dielectric multi-layer 632 while being transmitted through the third dielectric multi-layer 633, and is emitted from the second emission surface 62d by changing the traveling direction by approximately 90°.

As described above, the color synthesis optical device 60 according to the fifth embodiment is capable of synthesizing the G, B, R, A, and V color lights. That is, the light source device 3D is capable of supplying the G, B, R, A, and V color lights to one end of the light guide 4.

Here, in the fifth embodiment, the light source device 3D is operated in three operation modes of the white light mode and the NBI mode in the first embodiment described above, and the blood vessel emphasizing mode in the second embodiment described above, under the control of the control device 9.

Even in a case of adopting the light source device 3D according to the fifth embodiment described above, the same effects as those of the first and fourth embodiments described above are obtained.

Modification Example 5-1 of Fifth Embodiment

In the fifth embodiment described above, the positional relationship between the B light source unit 30 and the A light source unit 80 may be reversed. At this time, the positional relationship between the first and fourth dielectric multi-layers 631 and 634 is also reversed. Then, in the configuration, the G, V, and A heat radiators 22, 52, and 82 are disposed in the first cooling flow path FP1. In addition, the B and R heat radiators 32 and 42 are disposed in the second cooling flow path FP2.

Sixth Embodiment

Next, a sixth embodiment of the present disclosure will be described.

In the following description, the same reference numerals will be applied to the same configurations as those of the fifth embodiment described above, and the detailed description will be omitted or simplified.

Figure 7:
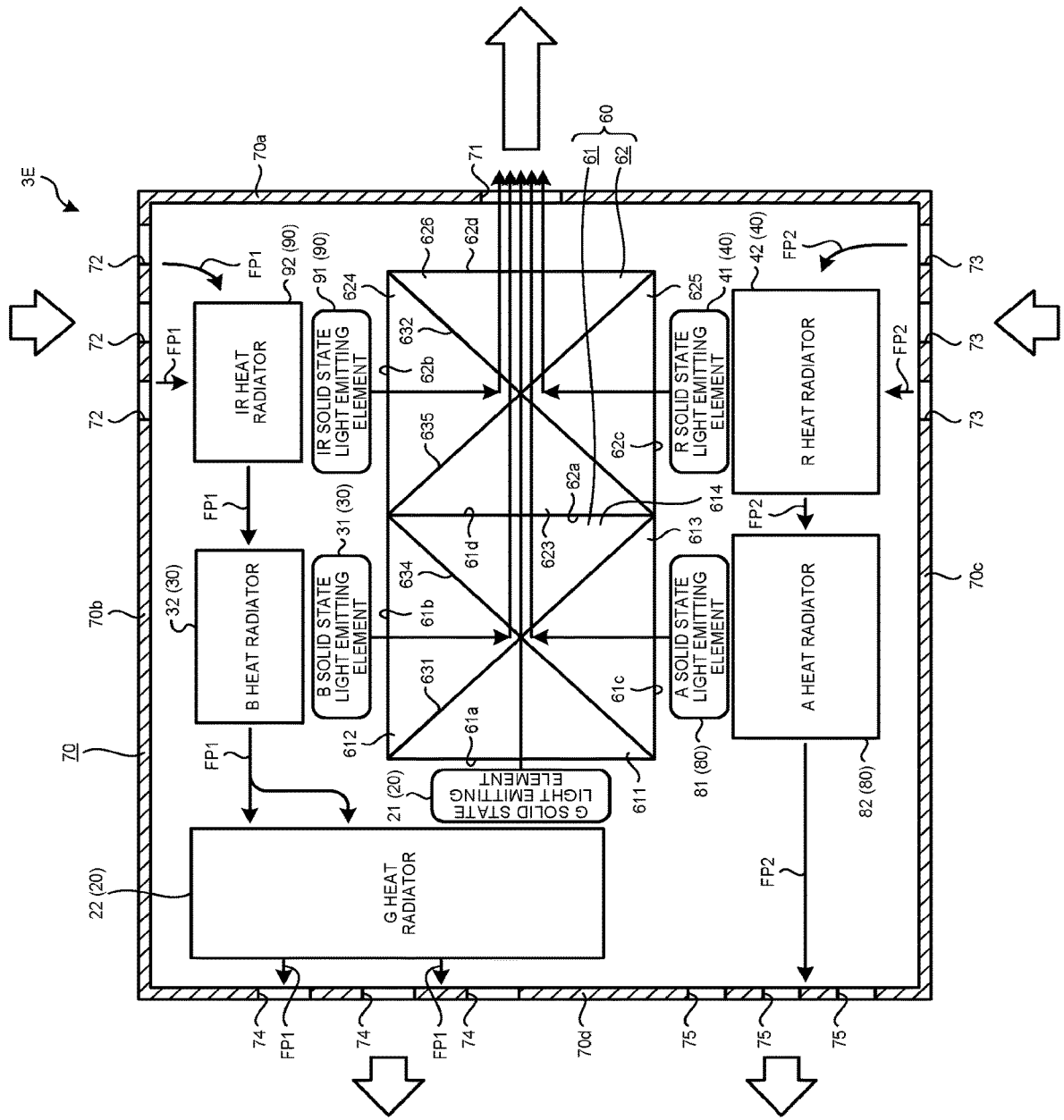
FIG. 7 is a diagram illustrating an internal configuration of a light source device according to a sixth embodiment.

FIG. 7 is a diagram illustrating an internal configuration of a light source device 3E according to the sixth embodiment.

In the sixth embodiment, as illustrated in FIG. 7, the light source device 3E is adopted instead of the light source device 3D (FIG. 6) in the fifth embodiment described above. Furthermore, the light source device 3E corresponds to the medical light source device according to the present disclosure.

Hereinafter, the configuration of the light source device 3E will be described with reference to FIG. 7.

In the light source device 3E, as with the fourth embodiment described above, the IR light source unit 90 is disposed in the disposing position of the V light source unit 50, with respect to the light source device 3D in the fifth embodiment described above. In the sixth embodiment, the IR solid state light emitting element 91 corresponds to the fifth solid state light emitting element according to the present disclosure. In addition, the IR color light corresponds to the fifth color light according to the present disclosure.

That is, in the sixth embodiment, as with the fourth embodiment described above, the G, B, and IR heat radiators 22, 32, and 92 are disposed in the first cooling flow path FP1.

In addition, in the light source device 3E, the IR solid state light emitting element 91 is disposed to face the fourth incidence surface 62b, and thus, the fifth dielectric multi-layer 635 is adopted instead of the third dielectric multi-layer 633, with respect to the light source device 3D in the fifth embodiment described above. In the sixth embodiment, the fifth dielectric multi-layer 635 corresponds to the fourth color separation surface according to the present disclosure.

Then, the G, B, and A color lights emitted from the first emission surface 61d, are incident on the second prism 62 from the abutting surface 62a, are transmitted through the second and fifth dielectric multi-layers 632 and 635, and are emitted from the second emission surface 62d. In addition, the IR color light emitted from the IR solid state light emitting element 91, is incident on the second prism 62 from the fourth incidence surface 62b, is reflected on the fifth dielectric multi-layer 635 while being transmitted through the second dielectric multi-layer 632, and is emitted from the second emission surface 62d by changing the traveling direction by approximately 90°. Further, the R color light emitted from the R solid state light emitting element 41, is incident on the second prism 62 from the fifth incidence surface 62c, is reflected on the second dielectric multi-layer 632 while being transmitted through the fifth dielectric multi-layer 635, and is emitted from the second emission surface 62d by changing the traveling direction by approximately 90°.

As described above, the color synthesis optical device 60 according to the sixth embodiment is capable of synthesizing the G, B, R, A, and IR color lights. That is, the light source device 3E is capable of supplying the G, B, R, A, and IR color lights to one end of the light guide 4.

Here, in the sixth embodiment, the light source device 3E is operated in three operation modes of the white light mode in the first embodiment described above, the blood vessel emphasizing mode in the second embodiment described above, and the fluorescent observation mode in the third embodiment described above, under the control of the control device 9.

Even in a case of adopting the light source device 3E according to the sixth embodiment described above, the same effects as those of the first and fourth embodiments described above are obtained.

Modification Example 6-1 of Sixth Embodiment

In the sixth embodiment described above, the positional relationship between the B light source unit 30 and the A light source unit 80 may be reversed. At this time, the positional relationship between the first and fourth dielectric multi-layers 631 and 634 is also reversed. Then, in the configuration, the G, A, and IR heat radiators 22, 82, and 92 are disposed in the first cooling flow path FP1. In addition, the B and R heat radiators 32 and 42 are disposed in the second cooling flow path FP2.

Seventh Embodiment

Next, a seventh embodiment of the present disclosure will be described.

In the following description, the same reference numerals will be applied to the same configurations as those of the sixth embodiment described above, and the detailed description will be omitted or simplified.

Figure 8:
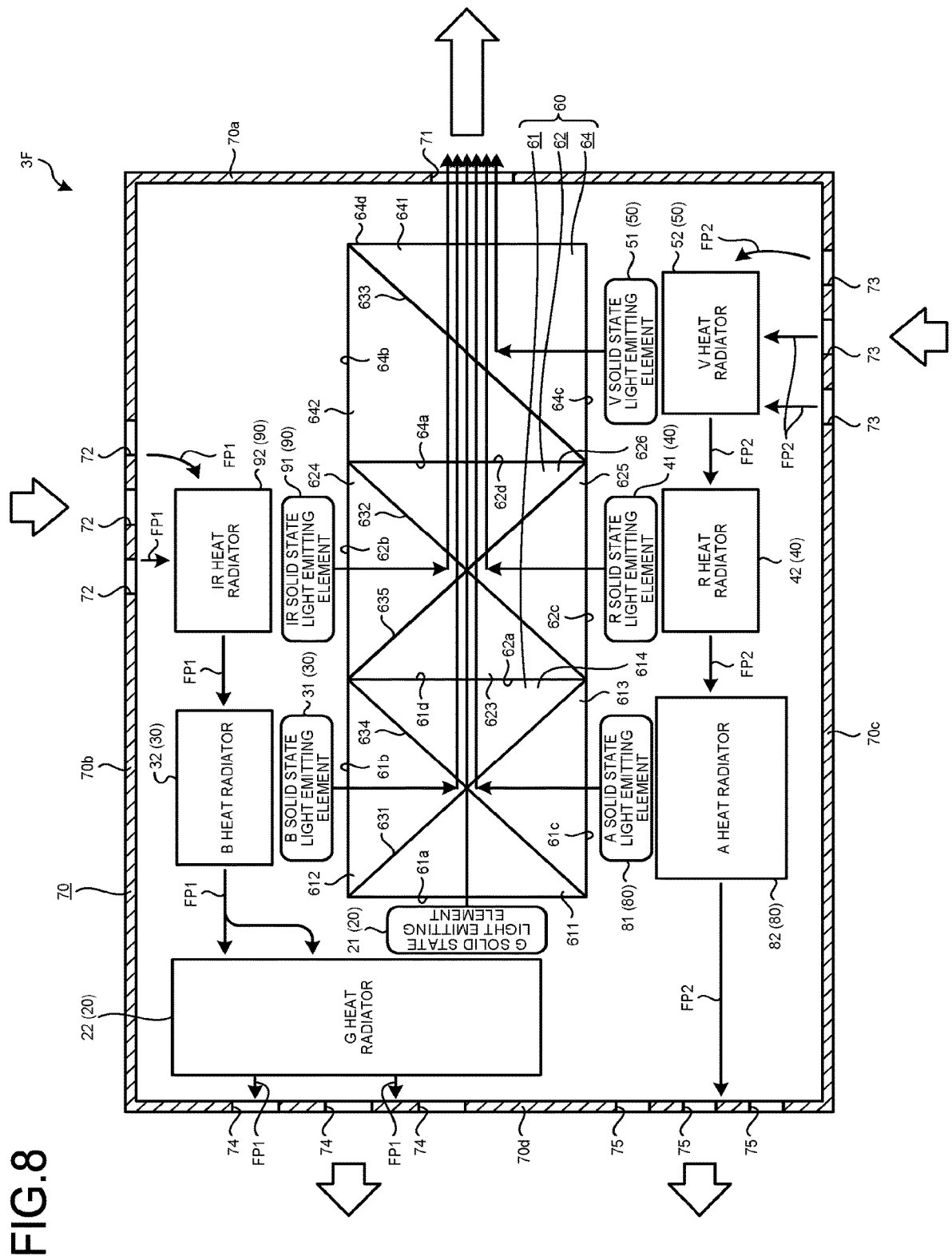
FIG. 8 is a diagram illustrating an internal configuration of a light source device according to a seventh embodiment.

FIG. 8 is a diagram illustrating an internal configuration of a light source device 3F according to the seventh embodiment.

In the seventh embodiment, as illustrated in FIG. 8, the light source device 3F is adopted instead of the light source device 3E (FIG. 7) in the sixth embodiment described above. Furthermore, the light source device 3F corresponds to the medical light source device according to the present disclosure.

Hereinafter, the configuration of the light source device 3F will be described with reference to FIG. 8.

In the light source device 3F, the V light source unit 50 is added, and a third prism 64 is added to the color synthesis optical device 60, with respect to the light source device 3E in the sixth embodiment described above.

The third prism 64 is approximately in the shape of a square in the plan view, in which two right angle prisms 641 and 642 are bonded together. Here, a planar shape of the third prism 64 is set to be identical to the planar shape of the first and second prisms 61 and 62. Then, the third prism 64 is arranged such that an outer surface corresponding to one side in four sides of an approximately square in the plan view, abuts on the second emission surface 62d, and is in the shape of a rectangle in the plan view, which extends in the right and left direction, along with the first and second prisms 61 and 62, in FIG. 8. In addition, the third prism 64 is arranged such that an interface in which the right angle prisms 641 and 642 are bonded together, is parallel to the second dielectric multi-layer 632. Furthermore, hereinafter, in the third prism 64, an outer surface abutting on the second emission surface 62d will be referred to as an abutting surface 64a, an outer surface obtained by extending the fourth incidence surface 62b will be referred to as a sixth incidence surface 64b, an outer surface obtained by extending the fifth incidence surface 62c will be referred to as a seventh incidence surface 64c, and an outer surface to be parallel to the abutting surface 64a will be referred to as a third emission surface 64d.

Then, the V solid state light emitting element 51 is arranged such that a front surface side faces the seventh incidence surface 64c through the optical system (not illustrated) such as a collimating lens provided between the seventh incidence surface 64c and the V solid state light emitting element 51. In the seventh embodiment, the V solid state light emitting element 51 corresponds to the fifth solid state light emitting element according to the present disclosure. In addition, the V color light corresponds to the fifth color light according to the present disclosure. Further, the IR solid state light emitting element 91 corresponds to a sixth solid state light emitting element according to the present disclosure. In addition, the IR color light corresponds to sixth color light according to the present disclosure.

That is, in the seventh embodiment, the R, V, and A heat radiators 42, 52, and 82 are disposed in the second cooling flow path FP2.

In addition, the third dielectric multi-layer 633 is formed on the interface in which the right angle prisms 641 and 642 are bonded together. In the seventh embodiment, the third dielectric multi-layer 633 corresponds to a fifth color separation surface according to the present disclosure.

Then, the G, B, R, A, and IR color lights emitted from the second emission surface 62d, are incident on the third prism 64 from the abutting surface 64a, are transmitted through the third dielectric multi-layer 633, and are emitted from the third emission surface 64d. In addition, the V color light emitted from the V solid state light emitting element 51, is incident on the third prism 64 from the seventh incidence surface 64c, is reflected on the third dielectric multi-layer 633, and is emitted from the third emission surface 64d by changing the traveling direction by approximately 90°.

As described above, the color synthesis optical device 60 according to the seventh embodiment is capable of synthesizing the G, B, R, V, A, and IR color lights. That is, the light source device 3F is capable of supplying the G, B, R, V, A, and IR color lights to one end of the light guide 4.

Here, in the seventh embodiment, the light source device 3F is operated in four operation modes of the white light mode and the NBI mode in the first embodiment described above, the blood vessel emphasizing mode in the second embodiment described above, and the fluorescent observation mode in the third embodiment described above, under the control of the control device 9.

Even in a case of adopting the light source device 3F according to the seventh embodiment described above, the same effects as those of the first and fourth embodiments described above are obtained.

Modification Example 7-1 of Seventh Embodiment

In the seventh embodiment described above, the positional relationship between the B light source unit 30 and the A light source unit 80 may be reversed. At this time, the positional relationship between the first and fourth dielectric multi-layers 631 and 634 is also reversed. Then, in the configuration, the G, A, and IR heat radiators 22, 82, and 92 are disposed in the first cooling flow path FP1. In addition, the B, R, and V heat radiators 32, 42, and 52 are disposed in the second cooling flow path FP2.

Modification Example 7-2 of Seventh Embodiment

In the seventh embodiment described above, the positional relationship between the V light source unit 50 and the IR light source unit 90 may be reversed. At this time, the positional relationship between the third and fifth dielectric multi-layers 633 and 635 is also reversed. Then, in the configuration, the G, B, and V heat radiators 22, 32, and 52 are disposed in the first cooling flow path FP1. In addition, the R, A, and IR heat radiators 42, 82, and 92 are disposed in the second cooling flow path FP2.

Modification Example 7-3 of Seventh Embodiment

In the seventh embodiment described above, the positional relationship between the B light source unit 30 and the A light source unit 80 may be reversed, and the positional relationship between the V light source unit 50 and the IR light source unit 90 may be reversed. At this time, the positional relationship between the first and fourth dielectric multi-layers 631 and 634, and the positional relationship between the third and fifth dielectric multi-layers 633 and 635 are also reversed. Then, in the configuration, the G, V, and A heat radiators 22, 52, and 82 are disposed in the first cooling flow path FP1. In addition, the B, R and IR heat radiators 32, 42, and 92 are disposed in the second cooling flow path FP2.

Modification Example 7-4 of Seventh Embodiment

In the seventh embodiment described above, the V light source unit 50 may be disposed in a disposing position of the IR light source unit 90, and the IR light source unit (the IR solid state light emitting element 91) may be disposed to face the sixth incidence surface 64b. At this time, the third dielectric multi-layer 633 is disposed in a disposing position of the fifth dielectric multi-layer 635, and the fifth dielectric multi-layer 635 is disposed in the third prism 64 to be parallel to the third dielectric multi-layer 633. Then, in the configuration, the G, B, V, and IR heat radiators 22, 32, 52, and 92 are disposed in the first cooling flow path FP1. In addition, the R and A heat radiators 42 and 82 are disposed in the second cooling flow path FP2.

Modification Example 7-5 of Seventh Embodiment

In Modification Example 7-4 described above, the positional relationship between the B light source unit 30 and the A light source unit 80 may be reversed. At this time, the positional relationship between the first and fourth dielectric multi-layers 631 and 634 is also reversed. Then, in the configuration, G, V, A, and IR heat radiators 22, 52, 82, and 92 are disposed in the first cooling flow path FP1. In addition, the B and R heat radiators 32 and 42 are disposed in the second cooling flow path FP2.

Modification Example 7-6 of Seventh Embodiment

In Modification Example 7-4 described above, the positional relationship between the V light source unit 50 and the IR light source unit 90 may be reversed. At this time, the positional relationship between the third and fifth dielectric multi-layers 633 and 635 is also reversed. Then, in the configuration, as with Modification Example 7-4 described above, the G, B, V, and IR heat radiators 22, 32, 52, and 92 are disposed in the first cooling flow path FP1. In addition, the R and A heat radiators 42 and 82 are disposed in the second cooling flow path FP2.

Modification Example 7-7 of Seventh Embodiment

In Modification Example 7-5 described above, the positional relationship between the V light source unit 50 and the IR light source unit 90 may be reversed. At this time, the positional relationship between the third and fifth dielectric multi-layers 633 and 635 is also reversed. Then, in the configuration, as with Modification Example 7-5 described above, the G, V, A, and IR heat radiators 22, 52, 82, and 92 are disposed in the first cooling flow path FP1. In addition, the B and R heat radiators 32 and 42 are disposed in the second cooling flow path FP2.

Figure 10:
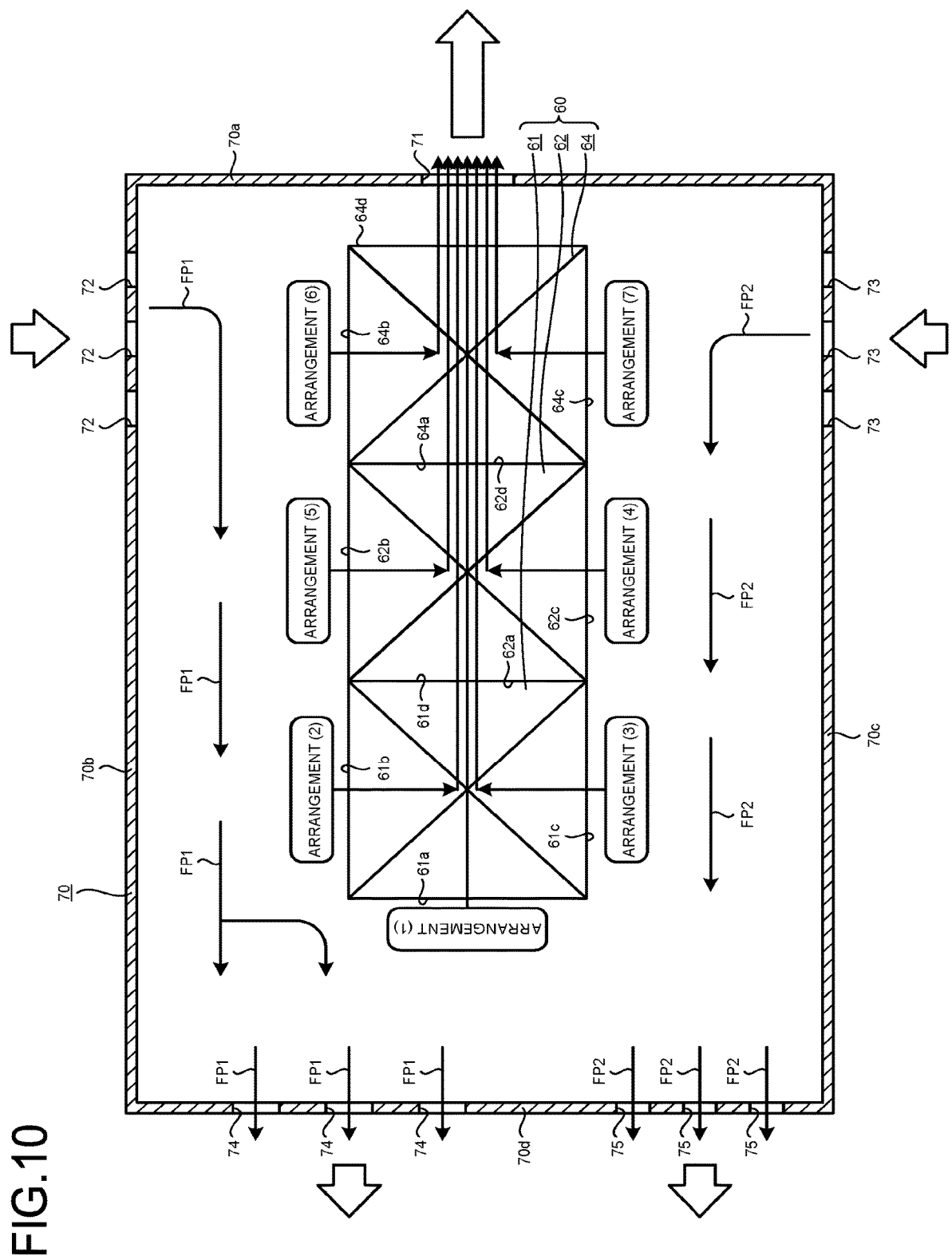
FIG. 10 is a diagram illustrating the arrangement pattern of the light source units of each of the first to seventh embodiments and Modification Examples 1-1, 2-1, 3-1, 4-1, 5-1, 6-1, and 7-1 to 7-7.

FIG. 9 and FIG. 10 are diagrams illustrating an arrangement pattern of each of the light source units 20, 30, 40, 50, 80, and 90 in the first to seventh embodiments and Modification Examples 1-1, 2-1, 3-1, 4-1, 5-1, 6-1, and 7-1 to 7-7. Furthermore, "G" illustrated in FIG. 9, indicates the G light source unit 20. "B" illustrated in FIG. 9, indicates the B light source unit 30. "R" illustrated in FIG. 9, indicates the R light source unit 40. "V" illustrated in FIG. 9, indicates the V light source unit 50. "A" illustrated in FIG. 9, indicates the A light source unit 80. "IR" illustrated in FIG. 9, indicates the IR light source unit 90. "-" illustrated in FIG. 9, indicates that any light source unit of the light source units 20, 30, 40, 50, 80, and 90 is not arranged. In addition, "Arrangement (1)" to "Arrangement (7)" illustrated in FIG. 9, correspond to "Arrangement (1)" to "Arrangement (7)" illustrated in FIG. 10. Here, Arrangements (1), (2), (5), and (6) are positioned in the first cooling flow path FP1. In addition, Arrangements (3), (4), and (7) are positioned in the second cooling flow path FP2.

The arrangement pattern of each of the light source units 20, 30, 40, 50, 80, and 90 in the first to seventh embodiments and Modification Examples 1-1, 2-1, 3-1, 4-1, 5-1, 6-1, and 7-1 to 7-7, described above, is as illustrated in FIG. 9 and FIG. 10.

Other Embodiments

The modes for carrying out the present disclosure have been described, but the present disclosure is not limited to the first to seventh embodiments and Modification Examples 1-1, 2-1, 3-1, 4-1, 5-1, 6-1, and 7-1 to 7-7 described above.

Figure 11:
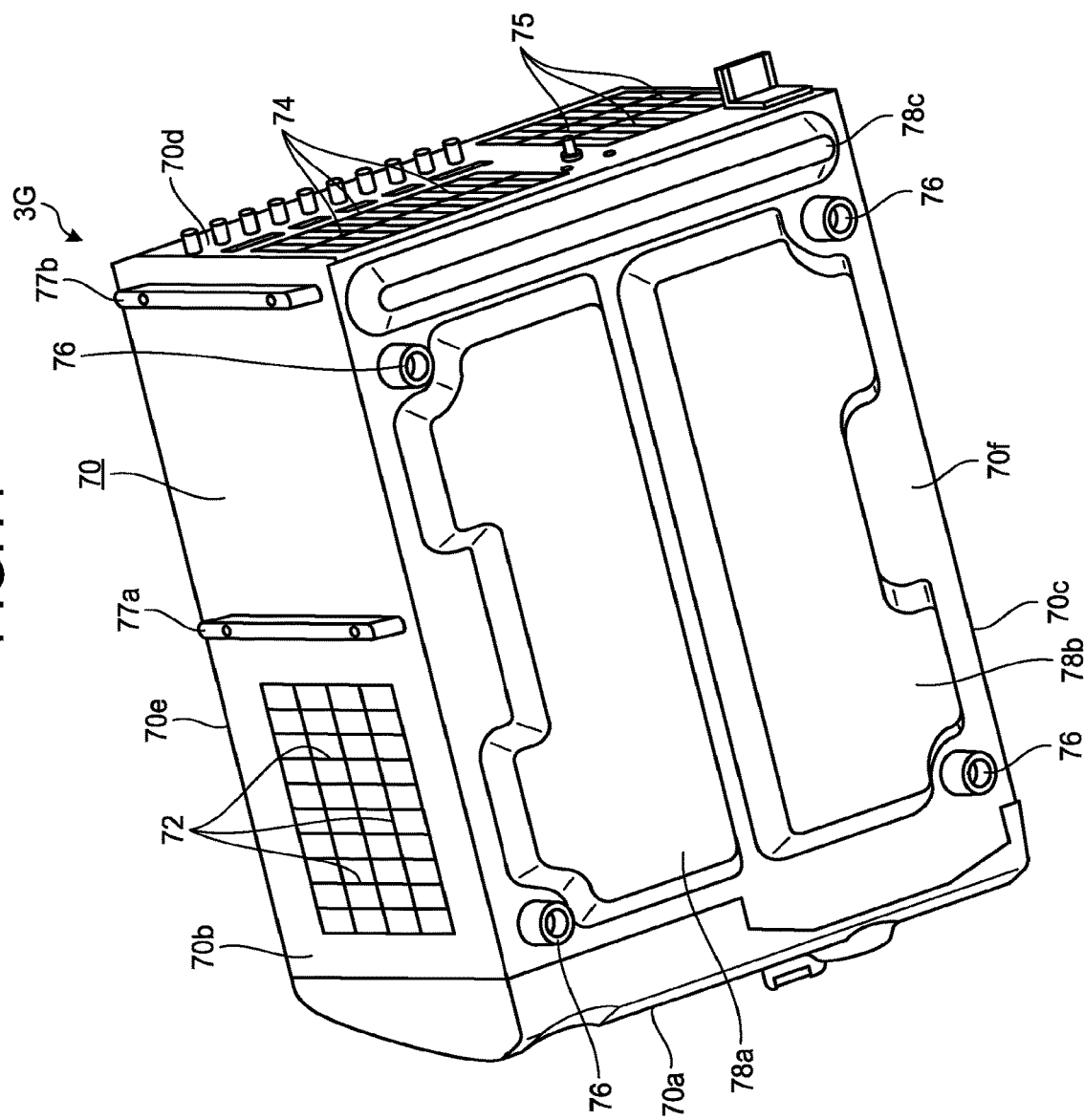
FIG. 11 is a diagram illustrating a modification example of the first to seventh embodiments.

FIG. 11 is a diagram illustrating a modification example of the first to seventh embodiments. Specifically, FIG. 11 is a diagram in which a light source device 3G according to this modification example is seen from the back lower side. Furthermore, the light source device 3G corresponds to the medical light source device according to the present disclosure.

Furthermore, in FIG. 11, in the outer casing 70, a side wall configuring a top surface is set to a top portion 70e, and a side wall configuring a bottom surface is set to a bottom portion 70f.

In the first to seventh embodiments and Modification Examples 1-1, 2-1, 3-1, 4-1, 5-1, 6-1, and 7-1 to 7-7 described above, as illustrated in FIG. 11, a structure may be adopted in which the air discharged from the first and second exhaust holes 74 and 75 (the air warmed in the outer casing 70) is prevented from being taken in from the first and second intake holes 72 and 73 through the first and second side wall portions 70*b* and 70*c* side or the bottom portion 70*f* side.

Specifically, as illustrated in FIG. 11, a pair of shielding members 77*a* and 77*b* is attached onto an outer surface of the first side wall portion 70*b*. Furthermore, even though it is not specifically illustrated, similarly, the pair of shielding members 77*a* and 77*b* is attached onto an outer surface of the second side wall portion 70*c*.

The pair of shielding members 77*a* and 77*b* is configured of elongated members which respectively protrude from the outer surface of the first side wall portion 70*b*, and respectively extend from the top portion 70*e* side to the bottom portion 70*f* side. Then, the pair of shielding members 77*a* and 77*b* is attached onto the outer surface of the first side wall portion 70*b* at a regular interval, on the back portion 70*d* side with respect to the first intake hole 72.

In addition, in the bottom portion 70*f*, as illustrated in FIG. 11, first to third bulge portions 78*a* to 78*c* are disposed by drawing or the like.

On the outer surface of the bottom portion 70*f*, the first and second bulge portions 78*a* and 78*b* are disposed over approximately the entire rectangular area surrounded by four leg portions 76 on the outer surface, and respectively have approximately the same height dimension as that of the leg portion 76 (a protruding dimension from the bottom portion 70*f*).

On the outer surface of the bottom portion 70*f*, the third bulge portion 78*c* is positioned on the back portion 70*d* side with respect to the first and second bulge portions 78*a* and 78*b*, and is formed to extend from the first side wall portion 70*b* side to the second side wall portion 70*c* side. Furthermore, the third bulge portion 78*c* has approximately the same height dimension as that of the leg portion 76.

Figure 12:
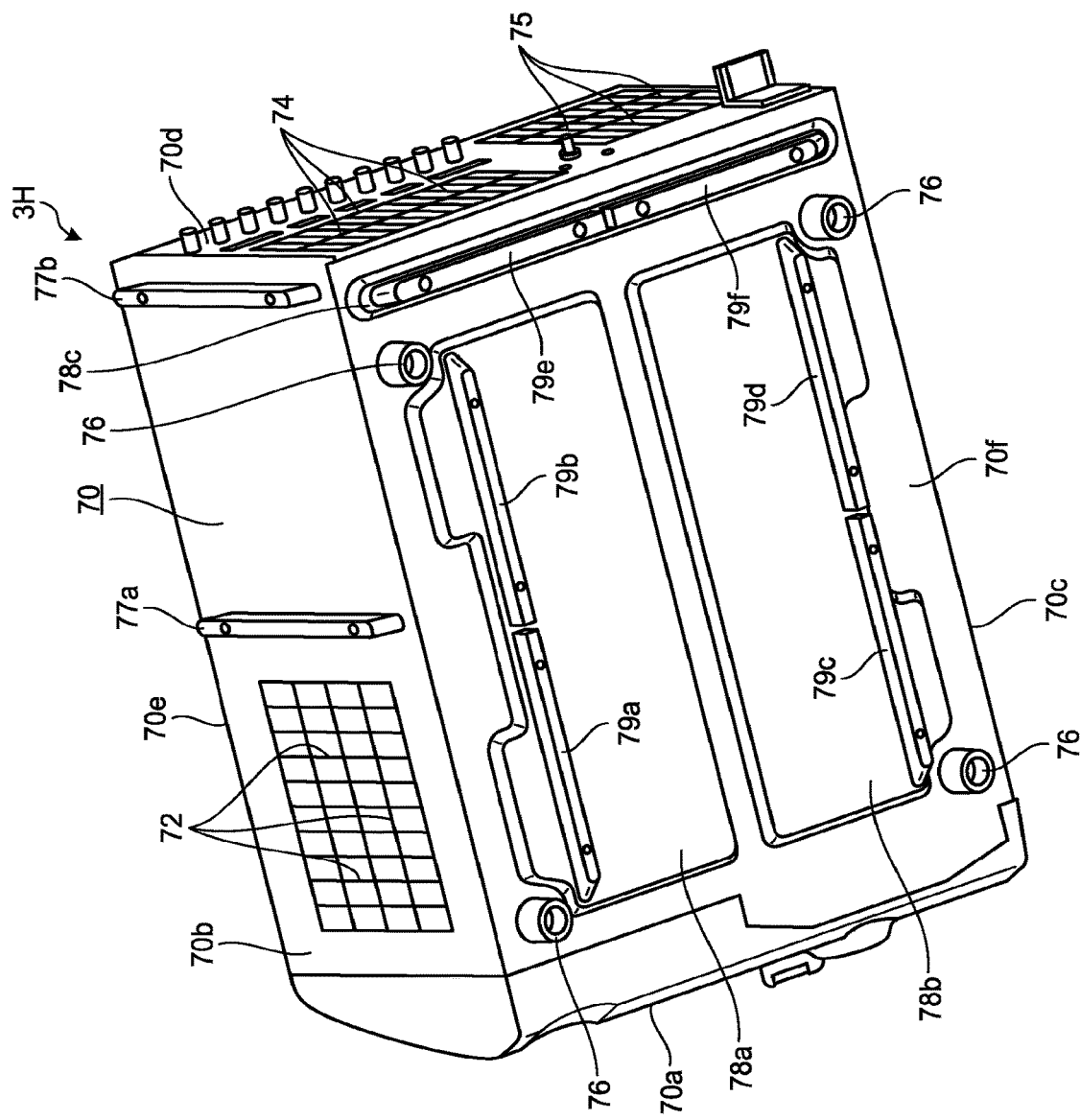
FIG. 12 is a diagram illustrating a modification example of the first to seventh embodiments.

FIG. 12 is a diagram illustrating a modification example of the first to seventh embodiments. Specifically, FIG. 12 is a diagram in which a light source device 3H according to this modification example is seen from the back lower side. Furthermore, the light source device 3H corresponds to the medical light source device according to the present disclosure.

In addition, in the modification example illustrated in FIG. 11, as illustrated in FIG. 12, the height dimension of the first to third bulge portions 78*a* to 78*c* may be set to be smaller than the height dimension of four leg portions 76, and in order to compensate the dimensional difference, shielding members 79*a* to 79*f* same as the shielding members 77*a* and 77*b* may be attached onto the first to third bulge portions 78*a* to 78*c*.

Figure 13:
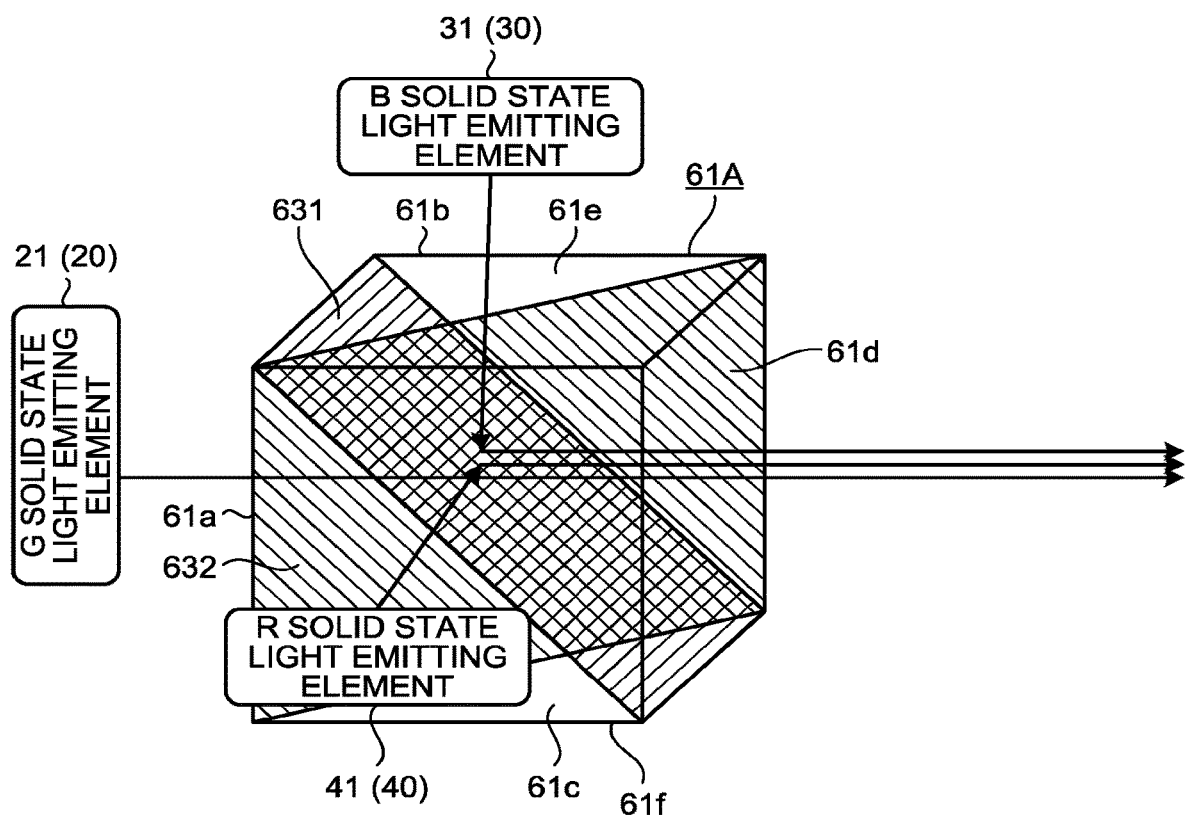
FIG. 13 is a diagram illustrating a modification example of the first to seventh embodiments.

FIG. 13 is a diagram illustrating a modification example of the first to seventh embodiments.

Furthermore, in FIG. 13, in a first prism 61A having the same outer shape as that of the first prism 61, a top surface is set to 61*e*, and a bottom surface is set to 61*f*.

In the first to seventh embodiments and Modification Examples 1-1, 2-1, 3-1, 4-1, 5-1, 6-1, and 7-1 to 7-7 described above, two dielectric multi-layers intersect with each other into the shape of X, but are not limited thereto, and for example, a configuration illustrated in FIG. 13 may be adopted, insofar as two dielectric multi-layers intersect with each other.

For example, in an example illustrated in FIG. 13, the first dielectric multi-layer 631 is disposed to extend from an edge portion between the first incidence surface 61*a* and the top surface 61*e* to an edge portion between the first emission surface 61*d* and the bottom surface 61*f*. On the other hand, the second dielectric multi-layer 632 is disposed to extend from an edge portion between the first and third incidence surfaces 61*a* and 61*c* to an edge portion between the second incidence surface 61*b* and the first emission surface 61*d*. Then, the G solid state light emitting element 21 is disposed to face the first incidence surface 61*a*. In addition, the B solid state light emitting element 31 is disposed to face the top surface 61*e*. Further, the R solid state light emitting element 41 is disposed to face the third incidence surface 61*c*.

Then, the G color light emitted from the G solid state light emitting element 21, is incident on the first prism 61A from the first incidence surface 61*a*, is transmitted through the first and second dielectric multi-layers 631 and 632, and is emitted from the first emission surface 61*d*. In addition, the B color light emitted from the B solid state light emitting element 31, is incident on the first prism 61A from the top surface 61*e*, is reflected on the first dielectric multi-layer 631 while being transmitted through the second dielectric multi-layer 632, and is emitted from the first emission surface 61*d* by changing the traveling direction by approximately 90°. Further, the R color light emitted from the R solid state light emitting element 41, is incident on the first prism 61A from the third incidence surface 61*c*, is reflected on the second dielectric multi-layer 632 while being transmitted through the first dielectric multi-layer 631, and is emitted from the first emission surface 61*d* by changing the traveling direction by approximately 90°.

In the first to seventh embodiments and Modification Examples 1-1, 2-1, 3-1, 4-1, 5-1, 6-1, and 7-1 to 7-7 described above, the first to fifth solid state light emitting elements according to the present disclosure are configured of an LED chip, but are not limited thereto, and may be configured of a laser diode.

In the first to seventh embodiments and Modification Examples 1-1, 2-1, 3-1, 4-1, 5-1, 6-1, and 7-1 to 7-7 described above, the G, B, R, V, A, and IR heat radiators 22, 32, 42, 52, 82, and 92 are respectively disposed to be close to the G, B, R, V, A, and IR solid state light emitting elements 21, 31, 41, 51, 81, and 91, but are not limited thereto. For example, the G, B, R, V, A, and IR heat radiators 22, 32, 42, 52, 82, and 92, and the G, B, R, V, A, and IR solid state light emitting elements 21, 31, 41, 51, 81, and 91 may be separated from each other, and may be respectively connected to each other by a heat pipe or the like, such that heat transfer can be performed.

In the first to seventh embodiments and Modification Examples 1-1, 2-1, 3-1, 4-1, 5-1, 6-1, and 7-1 to 7-7 described above, the color synthesis optical device 60 is configured by using the first to third prisms 61, 62, and 64, but is not limited thereto, and may be configured of a dichroic mirror without using a prism.

In the first to seventh embodiments and Modification Examples 1-1, 2-1, 3-1, 4-1, 5-1, 6-1, and 7-1 to 7-7 described above, a combination of the first to sixth color lights according to the present disclosure, is not limited to a combination of the G, B, R, V, A, and IR color lights, and the other combination may be adopted. In addition, a configuration using seven or more color lights having different peak wavelengths may be adopted.

In the first to seventh embodiments and Modification Examples 1-1, 2-1, 3-1, 4-1, 5-1, 6-1, and 7-1 to 7-7 described above, the first to fifth dielectric multi-layers 631 to 635 are configured of the highpass filter or the lowpass filter, but are not limited thereto, and may be configured of a bandpass filter.

In the first to seventh embodiments described above, the medical light source device according to the present disclosure is used for a rigid endoscope, but is not limited thereto.

For example, the medical light source device according to the present disclosure may be adopted to a flexible endoscope. In addition, the medical light source device according to the present disclosure may be adopted to a medical observation device performing imaging by enlarging a predetermined visual field range in the subject (in the living body) or on a front surface of the subject (on a front surface of the living body) (for example, refer to JP 2016-42981 A).

The medical light source device according to the present disclosure includes the color synthesis optical device capable of synthesizing the first to fourth color lights respectively emitted from the first to fourth solid state light emitting elements. The color synthesis optical device includes the first and second color separation surfaces disposed to intersect with each other, and the third color separation surface disposed on the light path latter stage of the first and second color separation surfaces. That is, the first and second color separation surfaces are disposed to intersect with each other, and thus, it is not necessary to juxtapose the second and third solid state light emitting elements along an emission light axis of the medical light source device, and it is possible to dispose the second and third solid state light emitting elements in approximately the same position in a direction along the emission light axis.

Therefore, according to the medical light source device of the present disclosure, it is possible to decrease a length dimension in the direction along the emission light axis, and to reduce the size.

In addition, the medical endoscopic device according to the present disclosure includes the medical light source device described above, and thus, the same action and effect as those of the medical light source device described above are obtained.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical light source device, comprising:
a first solid state light emitting element configured to emit first color light;
a second solid state light emitting element configured to emit second color light of which a peak wavelength is shorter than that of the first color light;
a third solid state light emitting element configured to emit third color light of which a peak wavelength is longer than that of the first color light;
a fourth solid state light emitting element configured to emit fourth color light of which a peak wavelength is shorter than that of the second color light or is longer than that of the third color light; and
a color synthesis optical device configured to synthesize the first color light, the second color light, the third color light, and the fourth color light,
wherein the color synthesis optical device includes
a first color separation surface configured to transmit the first color light and the third color light, and reflect the second color light,
a second color separation surface disposed to intersect with the first color separation surface, and configured to transmit the first color light and the second color light, and reflect the third color light, and
a third color separation surface disposed on a light path latter stage with respect to the first color separation surface and the second color separation surface, and configured to transmit the first color light, the second color light, and the third color Lilt, and reflect the fourth color light.

2. The medical light source device according to claim 1, wherein the peak wavelength of the fourth color light is longer than that of the third color light,
the medical light source device further includes
a fifth solid state light emitting element configured to emit fifth color light of which a peak wavelength is shorter than that of the second color light or is longer than that of the fourth color light,
the third color separation surface is configured to transmit the first color light, the second color light, the third color light, and the fifth color light, and
the color synthesis optical device includes
a fourth color separation surface disposed to intersect with the third color separation surface, and configured to transmit the first color light, the second color light, the third color light, and the fourth color light, and reflect the fifth color light.

3. The medical light source device according to claim 2, wherein the peak wavelength of the fifth color light is shorter than that of the second color light.

4. The medical light source device according to claim 1, wherein the peak wavelength of the fourth color light is longer than that of the third color light,
the medical light source device further includes
a fifth solid state light emitting element configured to emit fifth color light of which a peak wavelength is shorter than that of the second color light, and
a sixth solid state light emitting element configured to emit sixth color light of which a peak wavelength is longer than that of the fourth color light,
the third color separation surface is configured to transmit the first color light, the second color light, the third color light, and one color light of the fifth color light and the sixth color light, and
the color synthesis optical device includes
a fourth color separation surface disposed to intersect with the third color separation surface, and configured to transmit the first color light, the second color light, the third color light, and the fourth color light, and reflect the one color light, and
a fifth color separation surface disposed on a light path latter stage with respect to the third color separation surface and the fourth color separation surface, and configured to transmit the first color light, the second color light, the third color light, the fourth color light, and the one color light, and reflect a reflected color light that is a different one of the fifth color light and the sixth color light and is different than the one color light.

5. The medical light source device according to claim 4, wherein the one color light is the fifth color light, and the reflected color light is the sixth color light.

6. The medical light source device according to claim 1, further comprising:
an outer casing where the first solid state light emitting element, the second solid state light emitting element, the third solid state light emitting element, the fourth solid state light emitting element, and the color synthesis optical device are housed,
wherein in the outer casing, a first cooling flow path and a second cooling flow path independent from each other are respectively disposed, the first solid state light emitting element is configured to emit color light having a green wavelength band, one solid state light emitting element of the third solid state light emitting element and the fourth solid state light emitting element is configured to emit color light having a red wavelength band, the first solid state light emitting element is cooled by cooling air circulated through the first cooling flow path, and the one solid state light emitting element is cooled by cooling air circulated through the second cooling flow path.

7. The medical light source device according to claim 6, wherein the second solid state light emitting element is configured to emit color light having a blue wavelength band, and is cooled by cooling air circulated through the first cooling flow path.

8. The medical light source device according to claim 7, wherein the second solid state light emitting element and the one solid state light emitting element are disposed on one side and an other side sandwiching the color synthesis optical device, respectively.

9. The medical light source device according to claim 6, wherein at least a part of the first cooling flow path and at least a part of the second cooling flow path are disposed to be parallel to a center axis of the first color light on one side and an other side sandwiching the color synthesis optical device, respectively.

10. The medical light source device according to claim 6, wherein the outer casing includes an intake hole configured to take in the cooling air to an inside, and an exhaust hole configured to discharge the cooling air after following the first cooling flow path and the second cooling flow path to an outside, and the intake hole and the exhaust hole are respectively disposed at different side walls in the outer casing.

11. The medical light source device according to claim 1, wherein the color synthesis optical device is a dichroic prism in which a plurality of prisms are integrally incorporated.

12. A medical endoscopic device, comprising:

an endoscope configured to be inserted into a subject, and emit illumination light into the subject; and the medical light source device according to claim 1, the medical light source device being configured to supply the illumination light to the endoscope.

* * * * *